US005980898A

United States Patent [19]
Glenn et al.

[11] Patent Number: 5,980,898
[45] Date of Patent: Nov. 9, 1999

[54] ADJUVANT FOR TRANSCUTANEOUS IMMUNIZATION

[75] Inventors: Gregory M. Glenn; Carl R. Alving, both of Bethesda, Md.

[73] Assignee: The United States of America as represented by the U.S. Army Medical Research & Material Command, Washington, D.C.

[21] Appl. No.: 08/896,085

[22] Filed: Jul. 17, 1997

Related U.S. Application Data

[63] Continuation-in-part of application No. 08/749,164, Nov. 14, 1996.

[51] Int. Cl.[6] .................... A61K 39/00; C07K 14/005; C07K 14/195
[52] U.S. Cl. .................. 424/184.1; 424/449; 424/450; 424/236; 424/240.1; 424/241.1; 424/275.1; 530/363; 530/403
[58] Field of Search .................. 424/449, 450, 424/184.1, 236, 240.1, 241.1, 275.1; 530/363, 403

[56] References Cited

U.S. PATENT DOCUMENTS

| | | |
|---|---|---|
| 4,196,191 | 4/1980 | Almeida . |
| 4,455,142 | 6/1984 | Marins . |
| 4,484,923 | 11/1984 | Amkraut . |
| 4,876,278 | 10/1989 | Taylor . |
| 4,877,612 | 10/1989 | Berger . |
| 4,921,757 | 5/1990 | Wheatley . |
| 4,929,442 | 5/1990 | Powell . |
| 5,008,050 | 4/1991 | Cullis . |
| 5,059,421 | 10/1991 | Loughrey . |
| 5,169,637 | 12/1982 | Lenk . |
| 5,200,393 | 4/1993 | Weiner . |
| 5,256,422 | 10/1993 | Albert . |
| 5,260,066 | 11/1993 | Wood . |
| 5,326,790 | 7/1994 | Thornfeldt . |
| 5,332,576 | 7/1994 | Mantelle . |
| 5,340,588 | 8/1994 | Domb ..................... 424/450 |
| 5,352,449 | 10/1994 | Beltz . |
| 5,464,386 | 11/1995 | Hofmann . |
| 5,601,827 | 2/1997 | Collier . |
| 5,607,691 | 3/1997 | Hale . |
| 5,686,100 | 11/1997 | Wille ..................... 424/449 |

FOREIGN PATENT DOCUMENTS

| | | |
|---|---|---|
| 47099/89 | 6/1990 | Australia . |
| 92/03122 | 3/1992 | WIPO . |

OTHER PUBLICATIONS

Marinaro, M, et al., Mucosal effect of cholera toxin in mice results from induction of T helper 2 (Th2) cells and IL–4. J. Immunol. 155:4621–4629, 1995.
Kosecka, U, et al., Pertussis toxin stimulates hypersensitivity and enhances nerve–mediated antigen uptake in rat intestines. Am. J. Physiology. 267:G745–G753, 1994.
Alving, *Vaccine*, 4:166–172, 1986.
Alving, *Journal of Immunological Methods*, 140:1–13, 1991.
Alving, *Immunobiology*, 187:430–446, 1993.
Alving, *Annals of the New York Academy of Sciences*, 690:265–275, 1993.
Alving, *AIDS Research and Human Retroviruses*, 10:S91–S94, 1994.
Alving, *Immunological Reviews*, 145:5–31, 1995.
Egbaria, *Advanced Drug Delivery Reviews*, 5:287–300, 1990.
Fleisher, *Life Sciences*, 57:1293–1297, 1995.
Glenn, *Immunology Letters*, 47:73–78, 1995.
Gupta, *Vaccine*, 13:1263–1276, 1995.
de Haan, *Vaccine*, 13:1320–1324, 1995.
Korting, *Journal of the American Academy of Dermatology*, 25:1068–1071, 1991.
Korting, *British Journal of Dermatology*, 132:571–579, 1995.
Mengiardi, *Vaccine*, 13:1306–1315, 1995.
Mezei, *Life Sciences*, 26:1473–1477, 1980.
Moghimi, *Journal of Microencapsulation*, 10:155–162, 1993.
Norimatsu, *Vaccine*, 13:1325–1329, 1995.
Paul, *Vaccine Research*, 4:145–164, 1995.
Paul, *European Journal of Immunology*, 25:3521–3524, 1995.
Powers, *Vaccine*, 13:1330–1335, 1995.
Ranade, *Journal of Clinical Pharmacology*, 31:401–418, 1991.
Rao, *Infection and Immunity*, 63:2396–2402, 1995.
Sauzet, *Vaccine*, 13:1339–1345, 1995.
Schäfer–Korting, *Journal of the American Academy of Dermatology*, 21:1271–1275, 1989.
Verma, *Biochimica et Biophysica Acta*, 1066:229–238, 1991.
Verma, *Infection and Immunity*, 60:2438–2444, 1992.
Vutla, *Journal of Pharmaceutical Sciences*, 85:5–8, 1996.
Wang, *The Journal of Immunology*, 156:4079–4082, 1996.
Wang, *The Journal of Immunology*, 154:2784–2793, 1995.
Wassef, *Immunomethods*, 4:217–222, 1994.

(List continued on next page.)

*Primary Examiner*—David Saunders
*Assistant Examiner*—Mary Beth Tung
*Attorney, Agent, or Firm*—Pillsbury, Madison & Sutro LLP

[57] ABSTRACT

A transcutaneous immunization system delivers antigen to immune cells without perforation of the skin, and induces an immune response in an animal or human. The system uses an adjuvant, preferably an ADP-ribosylating exotoxin, to induce an antigen-specific immune response (e.g., humoral and/or cellular effectors) after transcutaneous application of a formulation containing antigen and adjuvant to intact skin of the animal or human. The efficiency of immunization may be enhanced by adding hydrating agents (e.g., liposomes), penetration enhancers, or occlusive dressings to the transcutaneous delivery system. This system may allow activation of Langerhans cells in the skin, migration of the Langerhans cells to lymph nodes, and antigen presentation.

13 Claims, 5 Drawing Sheets

OTHER PUBLICATIONS

Weiner, *Antimicrobial Agents and Chemotherapy,* 33:1217–1221, 1989.
White, *Vaccine,* 11:1341–1346, 1993.
White, *Vaccine,* 13:1111–1122, 1995.
Yasutomi, *Journal of Virology,* 69:2279–2284, 1995.
Zellmer, *Biochimica et Biophysica Acta,* 1237:176–182, 1995.
Alving, In: *Liposome Technology,* 2nd Ed. (Gregoriadis, ed.), CRC Press, pp. 317–343, 1993.
Small, In: *Handbook of Lipid Research,* Plenum, 4:43–87, 1986.
Small, In: *Handbook of Lipid Research,* Plunum, 4:89–96, 1986.
Becker, *Experimental Dermatology,* 2:63–69, 1993.
Blauvelt, *Journal of Investigative Dermatology,* 104:293–296, 1995.
Bowen, *Immunology,* 81:338–342, 1994.
Chin, *Veterinary Microbiology,* 43:21–32, 1995.
Chin, *Journal of Biotechnology,* 44:13–19, 1996.
Condon, *Nature Medicine,* 2:1122–1128, 1996.
Enk, *The Journal of Immunology,* 151:2390–2398, 1993.
Goodnow, *Immunological Reviews,* 156:5–10, 1997.
Knop, *International Archives of Allergy and Immunology,* 107:231–232, 1995.
Mahmoud, *Science,* 246:1015–1022, 1989.
Peters, *Immunology Today,* 17:273–278, 1996.
Schwarzenberger, *Journal of Investigative Dermatology,* 106:553–558, 1996.
Stacey, *The Journal of Immunology,* 157:2116–2122, 1996.
Steinman, *Immunological Reviews,* 156:25–37, 1997.
Stingl, *Immunological Series,* 46:3–72, 1989.
Udey, *Clinical and Experimental Immunology,* 107(suppl. 1):6–8, 1997.

5,980,898

ADJUVANT FOR TRANSCUTANEOUS IMMUNIZATION

CROSS-REFERENCE TO RELATED APPLICATIONS

This is a continuation in-part of U.S. application Ser. No. 08/749,164 filed Nov. 14, 1996.

GOVERNMENT RIGHTS

The U.S. government may retain certain rights in this invention.

BACKGROUND

The invention relates to transcutaneous immunization, and adjuvants useful therein, to induce an antigen-specific immune response.

Transcutaneous immunization requires both passage of an antigen through the outer barriers of the skin, which are normally impervious to such passage, and an immune response to the antigen. We showed in U.S. application Ser. No. 08/749,164 that using cholera toxin as an antigen elicits a strong antibody response that is highly reproducible; the antigen could be applied in a saline solution to the skin, with or without liposomes. In the present application, we show transcutaneous immunization using adjuvants such as, for example, bacterial exotoxins, their subunits, and related toxins.

There is a report of transdermal immunization with transferosomes by Paul et al. (1995). In this publication, the transferosomes are used as a carrier for proteins (bovine serum albumin and gap junction proteins) against which the complement-mediated lysis of antigen-sensitized liposomes is directed. An immune response was not induced when solution containing the protein was placed on the skin; only transferosomes were able to transport antigen across the skin and achieve immunization. As discussed in U.S. application Ser. No. 08/749,164, transferosomes are not liposomes.

FIG. 1 of Paul et al. (1995) showed that only a formulation of antigen and transferosomes induced an immune response, assayed by lysis of antigen-sensitized liposomes. Formulations of antigen in solution, antigen and mixed micelles, and antigen and liposomes (i.e., smectic mesophases) applied to the skin did not induce an immune response equivalent to that induced by subcutaneous injection. Therefore, there was a positive control (i.e., antigen and transfersomes) to validate their negative conclusion that a formulation of antigen and liposomes did not cause transdermal immunization.

Paul et al. (1995) stated on page 3521 that the skin is an effective protective barrier that is "impenetrable to substances with a molecular mass at most 750 DA", precluding non-invasive immunization with large immunogen through intact skin. Therefore, the reference would teach away from using a molecule like cholera toxin (which is 85,000 daltons) because such molecules would not be expected to penetrate the skin and, therefore, would not be expected to achieve immunization. Thus, skin represents a barrier that would make penetration by an adjuvant or antigen like cholera toxin unexpected without the disclosure of the present invention.

Paul and Cevc (1995) stated on page 145, "Large molecules normally do not get across the intact mammalian skin. It is thus impossible to immunize epicutaneously with simple peptide or protein solutions." They concluded, "The dermally applied liposomal or mixed micellar immunogens are biologically as inactive as simple protein solutions, whether or not they are combined with the immunoadjuvant lipid A."

Wang et al. (1996) placed a solution of ovalbumin (OVA) in water on the skin of shaved mice to induce an allergic type response as a model for atopic dermatitis. Mice were anesthetized and covered with an occlusive patch containing up to 10 mg of OVA, which was placed on the skin continuously for four days. This procedure was repeated after two weeks.

In FIG. 2 of Wang et al. (1996), an ELISA assay done to determine the IgG2a antibody response showed no IgG2a antibody response to OVA. However, IgE antibodies that are associated with allergic responses could be detected. In a further experiment, the mice were more extensively patched with OVA in solution for four days every two weeks. This was repeated five times, i.e., the mice wore patches for a total of 20 days. Again, the high dose of OVA did not produce significant IgG2a antibodies. Significant levels of IgE antibodies were produced.

The authors stated on page 4079 that "we established an animal model to show that epicutaneous exposure to protein Ag, in the absence of adjuvant, can sensitize animals and induce a dominant Th2-like response with high levels of IgE". Extensive epicutaneous exposure to high doses of protein antigen could not produce significant IgG antibodies but could induce IgE antibodies, the hallmark of an allergic type reaction. Thus, Wang et al. (1996) teaches that OVA exposure as described is a model for atopic dermatitis and not a mode of immunization. Therefore, following the teaching of the reference, one would have expected that transcutaneous immunization with antigen would induce high levels of IgE antibodies if it were to pass through the skin and induce an immune response. Instead, we have unexpectedly found that antigen placed on the skin in a saline solution with adjuvant induces high levels of IgG and some IgA, but not IgE.

In contrast to the cited references, the inventors have found that application to the skin of antigen and adjuvant provides a transcutaneous delivery system for antigen that can induce an antigen-specific immune response of IgG or IgA. The adjuvant is preferably an ADP-ribosylating exotoxin. Optionally, hydration, penetration enhancers, or occlusive dressings may be used in the transcutaneous delivery system.

SUMMARY OF THE INVENTION

An object of the invention is to provide a system for transcutaneous immunization that induces an immune response (e.g., humoral and/or cellular effectors) in an animal or human. The system provides simple application to intact skin of an organism of a formulation comprised of antigen and adjuvant to induce a specific immune response against the antigen. In particular, the adjuvant may activate antigen presenting cells of the immune system (e.g., Langerhans cells in the epidermis, dermal dendritic cells, dendritic cells, macrophages, B lymphocytes) and/or induce the antigen presenting cells to phagocytose the antigen. The antigen presenting cells then present the antigen to T and B cells. In the instance of Langerhans cells, the antigen presenting cells then may migrate from the skin to the lymph nodes and present antigen to lymphocytes (e.g., B and/or T cells), thereby inducing an antigen-specific immune response.

In addition to eliciting immune reactions leading to generation of an antigen-specific B lymphocyte and/or T lymphocyte, including a cytotoxic T lymphocyte (CTL), another object of the invention is to positively and/or negatively regulate components of the immune system by using the transcutaneous immunization system to affect antigen-specific helper (Th1 and/or Th2) or delayed-type hypersensitivity ($T_{DTH}$) T-cell subsets.

In a first embodiment of the invention, a formulation containing antigen and adjuvant is applied to intact skin of an organism, the antigen is presented to immune cells, and an antigen-specific immune response is induced without perforating the skin. The formulation may include additional antigens such that transcutaneous application of the formulation induces an immune response to multiple antigens. In such a case, the antigens may or may not be derived from the same source, but the antigens will have different chemical structures so as to induce immune responses specific for the different antigens. Antigen-specific lymphocytes may participate in the immune response and, in the case of participation by B lymphocytes, antigen-specific antibodies may be part of the immune response.

In a second embodiment of the invention, the above method is used to treat an organism. If the antigen is derived from a pathogen, the treatment vaccinates the organism against infection by the pathogen or against its pathogenic effects such as those caused by toxin secretion. A formulation that includes a tumor antigen may provide a cancer treatment; a formulation that includes an autoantigen may provide a treatment for a disease caused by the organism's own immune system (e.g., autoimmune disease).

In a third embodiment of the invention, a patch for use in the above methods is provided. The patch comprises a dressing, and effective amounts of antigen and adjuvant. The dressing may be occlusive or non-occlusive. The patch may include additional antigens such that application of the patch induces an immune response to multiple antigens. In such a case, the antigens may or may not be derived from the same source, but the antigens will have different chemical structures so as to induce an immune response specific for the different antigens. For effective treatment, multiple patches may be applied at frequent intervals or constantly over a period of time.

Moreover, in a fourth embodiment of the invention, the formulation is applied to intact skin overlying more than one draining lymph node field using either single or multiple applications. The formulation may include additional antigens such that application to intact skin induces an immune response to multiple antigens. In such a case, the antigens may or may not be derived from the same source, but the antigens will have different chemical structures so as to induce an immune response specific for the different antigens.

The products and methods may be used therapeutically to treat existing disease, protectively to prevent disease, or to reduce the severity and/or duration of disease.

In addition to antigen and adjuvant, the formulation may comprise a hydrating agent (e.g., liposomes), a penetration enhancer, or both. For example, the formulation may comprise AQUAPHOR (an emulsion of petrolatum, mineral oil, mineral wax, wool wax, panthenol, bisabol, and glycerin), emulsions (e.g., aqueous creams), oil-in-water emulsions (e.g., oily creams), anhydrous lipids and oil-in-water emulsions, anhydrous lipids and water-in-oil emulsions, fats, waxes, oil, silicones, and humectants (e.g., glycerol).

The antigen may be derived from a pathogen that can infect the organism (e.g., bacterium, virus, fungus, or parasite), or a cell (e.g., tumor cell or normal cell). The antigen may be a tumor antigen or an autoantigen. Chemically, the antigen may be a carbohydrate, glycolipid, glycoprotein, lipid, lipoprotein, phospholipid, polypeptide, or chemical or recombinant conjugate of the above. The molecular weight of the antigen may be greater than 500 daltons, preferably greater than 800 daltons, and more preferably greater than 1000 daltons.

Antigen may be obtained by recombinant means, chemical synthesis, or purification from a natural source. Preferred are proteinaceous antigen or conjugates with polysaccharide. Antigen may be at least partially purified in cell-free form. Alternatively, antigen may be provided in the form of a live virus, an attenuated live virus, or an inactivated virus.

Inclusion of an adjuvant may allow potentiation or modulation of the immune response. Moreover, selection of a suitable antigen or adjuvant may allow preferential induction of a humoral or cellular immune response, specific antibody isotypes (e.g., IgM, IgD, IgA1, IgA2, IgE, IgG1, IgG2, IgG3, and/or IgG4), and/or specific T-cell subsets (e.g., CTL, Th1, Th2 and/or $T_{DTH}$).

Preferably, the adjuvant is an ADP-ribosylating exotoxin or a subunit thereof. Optionally, an activator of Langerhans cells may be used.

Optionally, antigen, adjuvant, or both may be provided in the formulation by means of a nucleic acid (e.g., DNA, RNA, cDNA, cRNA) encoding the antigen or adjuvant as appropriate.

This technique is called genetic immunization.

The term "antigen" as used in the invention, is meant to describe a substance that induces a specific immune response when presented to immune cells of an organism. An antigen may comprise a single immunogenic epitope, or a multiplicity of immunogenic epitopes recognized by a B-cell receptor (i.e., antibody on the membrane of the B cell) or a T-cell receptor. A molecule may be both an antigen and an adjuvant (e.g., cholera toxin) and, thus, the formulation may contain only one component.

The term "adjuvant" as used in the invention, is meant to describe a substance added to the formulation to assist in inducing an immune response to the antigen.

The term "effective amount" as used in the invention, is meant to describe that amount of antigen which induces an antigen-specific immune response. Such induction of an immune response may provide a treatment such as, for example, immunoprotection, desensitization, immunosuppression, modulation of autoimmune disease, potentiation of cancer immunosurveillance, or therapeutic vaccination against an established infectious disease.

The term "draining lymph node field" as used in the invention means an anatomic area over which the lymph collected is filtered through a set of defined set of lymph nodes (e.g., cervical, axillary, inguinal, epitrochelear, popliteal, those of the abdomen and thorax).

BRIEF DESCRIPTION OF THE DRAWINGS

FIG. 1 shows cholera toxin (CT) induces enhanced major histocompatibility complex (MHC) class II expression on Langerhans cells (LC), changes in LC morphology, and loss of LCs (presumably through migration). BALB/c mice (H-$2^d$) were transcutaneously immunized with cholera CT or its B subunit (CTB) in saline solution on the ear (7,000 anti-CT ELISA units after a single immunization). Previous experiments had established that mice were readily immunized when using the skin of the ear. After 16 hours, epidermal sheets were prepared and stained for MHC class II molecules (scale bar is 50 $\mu$m). Panels indicate (A) saline alone as a negative control, (B) transcutaneous immunization with CT in saline, (C) transcutaneous immunization with CTB in saline, and (D) intradermal injection with tumor necrosis factor-α (10 μg) as a positive control.

DETAILED DESCRIPTION OF THE INVENTION

Figure 1A:
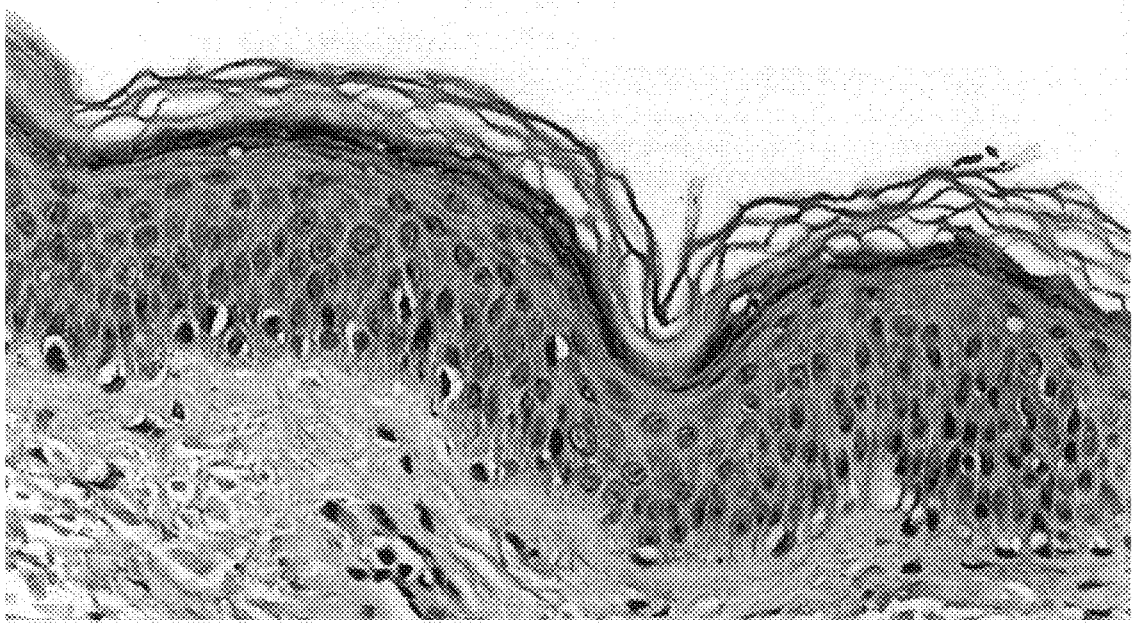

A transcutaneous immunization system delivers agents to specialized cells (e.g., antigen presentation cell, lymphocyte) that produce an immune response (Bos, 1997). These agents as a class are called antigens. Antigen may be composed of chemicals such as, for example, carbohydrate, glycolipid, glycoprotein, lipid, lipoprotein, phospholipid, polypeptide, conjugates thereof, or any other material known to induce an immune response. Antigen may be provided as a whole organism such as, for example, a bacterium or virion; antigen may be obtained from an extract or lysate, either from whole cells or membrane alone; or antigen may be chemically synthesized or produced by recombinant means.

Processes for preparing a pharmaceutical formulation are well-known in the art, whereby the antigen and adjuvant is combined with a pharmaceutically acceptable carrier vehicle. Suitable vehicles and their preparation are described, for example, in Remington's Pharmaceutical Sciences by E. W. Martin. Such formulations will contain an effective amount of the antigen and adjuvant together with a suitable amount of vehicle in order to prepare pharmaceutically acceptable compositions suitable for administration to a human or animal. The formulation may be applied in the form of an cream, emulsion, gel, lotion, ointment, paste, solution, suspension, or other forms known in the art. In particular, formulations that enhance skin hydration, penetration, or both are preferred. There may also be incorporated other pharmaceutically acceptable additives including, for example, diluents, binders, stabilizers, preservatives, and colorings.

Increasing hydration of the stratum corneum will increase the rate of percutaneous absorbtion of a given solute (Roberts and Walker, 1993). As used in the present invention, "penetration enhancer" does not include substances such as, for example: water, physiological buffers, saline solutions, and alcohols which would not perforate the skin.

An object of the present invention is to provide a novel means for immunization through intact skin without the need for perforating the skin. The transcutaneous immunization system provides a method whereby antigens and adjuvant can be delivered to the immune system, especially specialized antigen presentation cells underlying the skin such as, for example, Langerhans cells.

Without being bound to any particular theory but only to provide an explanation for our observations, it is presumed that the transcutaneous immunization delivery system carries antigen to cells of the immune system where an immune response is induced. The antigen may pass through the normal protective outer layers of the skin (i.e., stratum corneum) and induce the immune response directly, or through an antigen presenting cell (e.g., macrophage, tissue macrophage, Langerhans cell, dendritic cell, dermal dendritic cell, B lymphocyte, or Kupffer cell) that presents processed antigen to a T lymphocyte. Optionally, the antigen may pass through the stratum corneum via a hair follicle or a skin organelle (e.g., sweat gland, oil gland).

Transcutaneous immunization with bacterial ADP-ribosylating exotoxins (bAREs) may target the epidermal Langerhans cell, known to be among the most efficient of the antigen presenting cells (APCs) (Udey, 1997). We have found that bAREs activate Langerhans cells when applied epicutaneously to the skin in saline solution. The Langerhans cells direct specific immune responses through phagocytosis of the antigens, and migration to the lymph nodes where they act as APCs to present the antigen to lymphocytes (Udey, 1997), and thereby induce a potent antibody response. Although the skin is generally considered a barrier to invading organisms, the imperfection of this barrier is attested to by the numerous Langerhans cells distributed throughout the epidermis that are designed to orchestrate the immune response against organisms invading via the skin (Udey, 1997).

According to Udey (1997):

"Langerhans cells are bone-marrow derived cells that are present in all mammalian stratified squamous epithelia. They comprise all of the accessory cell activity that is present in uninflammed epidermis, an in the current paradigm are essential for the initiation and propagation of immune responses directed against epicutaneously applied antigens. Langerhans cells are members of a family of potent accessory cells ('dendritic cells') that are widely distributed, but infrequently represented, in epithelia and solid organs as well as in lymphoid tissue . . .

"It is now recognized that Langerhans cells (and presumably other dendritic cells) have a life cycle with at least two distinct stages. Langerhans cells that are located in epidermis constitute a regular network of antigen-trapping 'sentinel' cells. Epidermal Langerhans cells can ingest particulates, including microorganisms, and are efficient processors of complex antigens. However, they express only low levels of MHC class I and II antigens and costimulatory molecules (ICAM-1, B7-1 and B7-2) and are poor stimulators of unprimed T cells. After contact with antigen, some Langerhans cells become activated, exit the epidermis and migrate to T-cell-dependent regions of regional lymph nodes where they local as mature dendritic cells. In the course of exiting the epidermis and migrating to lymph nodes, antigen-bearing epidermal Langerhans cells (now the 'messengers') exhibit dramatic changes in morphology, surface phenotype and function. In contrast to epidermal Langerhans cells, lymphoid dendritic cells are essentially non-phagocytic and process protein antigens inefficiently, but express high levels of MHC class I and class II antigens and various costimulatory molecules and are the most potent stimulators of naive T cells that have been identified."

We envision that the potent antigen presenting capability of the epidermal Langerhans cells can be exploited for transcutaneously delivered vaccines. A transcutaneous immune response using the skin immune system would require delivery of vaccine antigen only to Langerhans cells in the stratum corneum (the outermost layer of the skin consisting of cornified cells and lipids) via passive diffusion and subsequent activation of the Langerhans cells to take up antigen, migrate to B-cell follicles and/or T-cell dependent regions, and present the antigen to B and/or T cells (Stingl et al., 1989). If antigens other that bAREs (for example BSA) were to be phagocytosed by the Langerhans cells, then these antigens could also be taken to the lymph node for presentation to T-cells and subsequently induce an immune response specific for that antigen (e.g., BSA). Thus, a feature of transcutaneous immunization is the activation of the Langerhans cell, presumably by a bacterial ADP-ribosylating exotoxin, ADP-ribosylating exotoxin binding subunits (e.g., cholera toxin B subunit), or other Langerhans cell activating substance.

The mechanism of transcutaneous immunization via Langerhans cells activation, migration and antigen presentation is clearly shown by the upregulation of MHC class II expression in the epidermal Langerhans cells from epidermal sheets transcutaneously immunized with CT or CTB. In addition, the magnitude of the antibody response induced by transcutaneous immunization and isotype switching to predominantly IgG is generally achieved with T-cell help (Janeway and Travers, 1996), and activation of both Th1 and Th2 pathways is suggested by the production of IgG1 and IgG2a (Paul and Seder, 1994; Seder and Paul, 1994). Alternatively, a large antibody response may be induced by a thymus-independent antigen type 1 (TI-1) which directly activates the B cell (Janeway and Travers, 1996).

The spectrum of more commonly known skin immune responses is represented by contact dermatitis and atopy. Contact dermatitis, a pathogenic manifestation of LC activation, is directed by Langerhans cells which phagocytose antigen, migrate to lymph nodes, present antigen, and sensitize T cells for the intense destructive cellular response that occurs at the affected skin site (Dahl, 1996; Leung, 1997). Atopic dermatitis may utilize the Langerhans cell in a similar fashion, but is identified with Th2 cells and is generally associated with high levels of IgE antibody (Dahl, 1996; Leung, 1997).

Transcutaneous immunization with cholera toxin and related bAREs on the other hand is a novel immune response with an absence of superficial and microscopic post-immunization skin findings (i.e., non-inflamed skin) shown by the absence of lymphocyte infiltration 24, 48 and 120 hours after immunization. This indicates that Langerhans cells "comprise all of the accessory cell activity that is present in uninflammed epidermis, and in the current paradigm are essential for the initiation and propagation of immune responses directed against epicutaneously applied antigens" (Udey, 1997). The uniqueness of the transcutaneous immune response here is also indicated by the both high levels of antigen-specific IgG antibody, and the type of antibody produced (e.g., IgM, IgG1, IgG2a, IgG2b, IgG3 and IgA) and the absence of anti-CT IgE antibody.

Thus, we have found that bacterial-derived toxins applied to the surface of the skin can activate Langerhans cells and induce a potent immune response manifested as high levels of antigen-specific circulating IgG antibodies. Such adjuvants may be used in transcutaneous immunization to enhance the IgG antibody response to proteins not otherwise immunogenic by themselves when placed on the skin.

Transcutaneous targeting of Langerhans cells may also be used to deactivate their antigen presenting function, thereby preventing immunization or sensitization. Techniques to deactivate Langerhans cells include, for example, the use of interleukin-10 (Peguet-Navarro et al., 1995), monoclonal antibody to interleukin-1β (Enk et al., 1993), or depletion via superantigens such as through staphylococcal enterotoxin-A (SEA) induced epidermal Langerhans cell depletion (Shankar et al., 1996).

Transcutaneous immunization may be induced via the ganglioside GM1 binding activity of CT, LT or subunits such as CTB (Craig and Cuatrecasas, 1975). Ganglioside GM1 is a ubiquitous cell membrane glycolipid found in all mammalian cells (Plotkin and Mortimer, 1994). When the pentameric CT B subunit binds to the cell surface a hydrophilic pore is formed which allows the A subunit to penetrate across the lipid bilayer (Ribi et al., 1988).

We have shown that transcutaneous immunization by CT or CTB may require ganglioside GM1 binding activity. When mice were transcutaneously immunized with CT, CTA and CTB, only CT and CTB resulted in an immune response. CTA contains the ADP-ribosylating exotoxin activity but only CT and CTB containing the binding activity were able to induce an immune response indicating that the B subunit was necessary and sufficient to immunize through the skin. We conclude that the Langerhans cell may be activated by CTB binding to its cell surface.

Antigen

Antigen of the invention may be expressed by recombinant means, preferably as a fusion with an affinity or epitope tag (Summers and Smith, 1987; Goeddel, 1990; Ausubel et al., 1996); chemical synthesis of an oligopeptide, either free or conjugated to carrier proteins, may be used to obtain antigen of the invention (Bodanszky, 1993; Wisdom, 1994). Oligopeptides are considered a type of polypeptide.

Oligopeptide lengths of 6 residues to 20 residues are preferred. Polypeptides may also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

Antigen obtained through recombinant means or peptide synthesis, as well as antigen of the invention obtained from natural sources or extracts, may be purified by means of the antigen's physical and chemical characteristics, preferably by fractionation or chromatography (Janson and Ryden, 1989; Deutscher, 1990; Scopes, 1993).

A multivalent antigen formulation may be used to induce an immune response to more than one antigen at the same time. Conjugates may be used to induce an immune response to multiple antigens, to boost the immune response, or both. Additionally, toxins may be boosted by the use of toxoids, or toxoids boosted by the use of toxins. Transcutaneous immunization may be used to boost responses induced initially by other routes of immunization such as by injection, or the oral or intranasal routes.

Antigen includes, for example, toxins, toxoids, subunits thereof, or combinations thereof (e.g., cholera toxin, tetanus toxoid).

Antigen may be solubilized in a buffer. Suitable buffers include, but are not limited to, phosphate buffered saline $Ca^{++}/Mg^{++}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH may be used as a diluent after solubilization in dilute acetic acid. Glycerol may be a suitable non-aqueous buffer for use in the present invention.

Hydrophobic antigen can be solubilized in a detergent, for example a polypeptide containing a membrane-spanning domain. Furthermore, for formulations containing liposomes, an antigen in a detergent solution (e.g., a cell membrane extract) may be mixed with lipids, and liposomes then may be formed by removal of the detergent by dilution, dialysis, or column chromatography. Certain antigens such as, for example, those from a virus (e.g., hepatitis A) need not be soluble per se, but can be incorporated directly into a liposome in the form of a virosome (Morein and Simons, 1985).

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, or parasite).

Bacteria include, for example: anthrax, campylobacter, cholera, diphtheria, enterotoxigenic *E. coli*, giardia, gonococcus, *Helicobacter pylori* (Lee and Chen, 1994), Hemophilus influenza B, Hemophilus influenza non-typable, meningococcus, pertussis, pneumococcus, salmonella, shigella, Streptococcus B, tetanus, *Vibrio cholerae*, and yersinia.

Viruses include, for example: adenovirus, dengue serotypes 1 to 4 (Delenda et al., 1994; Fonseca et al., 1994; Smucny et al., 1995), ebola (Jahrling et al., 1996), enterovirus, hepatitis serotypes A to E (Blum, 1995; Katkov, 1996; Lieberman and Greenberg, 1996; Mast, 1996; Shafara et al., 1995; Smedila et al., 1994; U.S. Pat. Nos. 5,314,808 and 5,436,126), herpes simplex virus 1 or 2, human immunodeficiency virus (Deprez et al., 1996), influenza, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever.

Parasites include, for example: *Entamoeba histolytica* (Zhang et al., 1995); Plasmodium (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), Leishmania (Frankenburg et al., 1996), and the Helminthes.

Adjuvant

The formulation also contains an adjuvant, although a single molecule may contain both adjuvant and antigen properties (e.g., cholera toxin) (Elson and Dertzbaugh, 1994). Adjuvants are substances that are used to specifically or non-specifically potentiate an antigen-specific immune response. Usually, the adjuvant and the formulation are mixed prior to presentation of the antigen but, alternatively, they may be separately presented within a short interval of time.

Adjuvants include, for example, an oil emulsion (e.g., complete or incomplete Freund's adjuvant), a chemokine (e.g., defensins 1 or 2, RANTES, MIP1-$\alpha$, MIP-2, interleukin-8) or a cytokine (e.g., interleukin-1$\beta$, -2, -6, -10 or -12; $\gamma$-interferon; tumor necrosis factor-$\alpha$; or granulocyte-monocyte-colony stimulating factor) (reviewed in Nohria and Rubin, 1994), a muramyl dipeptide derivative (e.g., murabutide, threonyl-MDP or muramyl tripeptide), a heat shock protein or a derivative, a derivative of Leishmania major LeIF (Skeiky et al., 1995), cholera toxin or cholera toxin B, a lipopolysaccharide (LPS) derivative (e.g., lipid A or monophosphoryl lipid A), or superantigen (Saloga et al., 1996). Also, see Richards et al. (1995) for adjuvants useful in immunization.

An adjuvant may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$) (Glenn et al., 1995).

Cholera toxin is a bacterial exotoxin from the family of ADP-ribsoylating exotoxins (referred to as bAREs). Most bAREs are organized as A:B dimer with a binding B subunit and an A subunit containing the ADP-ribosyltransferase. Such toxins include diphtheria, Pseudomonas exotoxin A, cholera toxin (CT), *E. coli* heat-labile enterotoxin (LT), pertussis toxin, *C. botulinum* toxin C2, *C. botulinum* toxin C3, *C. limosum* exoenzyme, *B. cereus* exoenzyme, Pseudomonas exotoxin S, *Staphylococcus aureus* EDIN, and *B. sphaericus* toxin.

Cholera toxin is an example of a bARE that is organized with A and B subunits. The B subunit is the binding subunit and consists of a B-subunit pentamer which is non-covalently bound to the A subunit. The B-subunit pentamer is arranged in a symmetrical doughnut-shaped structure that binds to $GM_1$-ganglioside on the target cell. The A subunit serves to ADP ribosylate the alpha subunit of a subset of the hetero trimeric GTP proteins (G proteins) including the Gs protein which results in the elevated intracellular levels of cyclic AMP. This stimulates release of ions and fluid from intestinal cells in the case of cholera.

Cholera toxin (CT) and its B subunit (CTB) have adjuvant properties when used as either an intramuscular or oral immunogen (Elson and Dertzbaugh, 1994; Trach et al., 1997). Another antigen, heat-labile enterotoxin from *E. coli* (LT) is 80% homologous at the amino acid level with CT and possesses similar binding properties; it also appears to bind the $GM_1$-ganglioside receptor in the gut and has similar ADP-ribosylating exotoxin activities. Another bARE, Pseudomonas exotoxin A (ETA), binds to the $\alpha_2$-macroglobulin receptor-low density lipoprotein receptor-related protein (Kounnas et al., 1992). bAREs are reviewed by Krueger and Barbieri (1995).

The examples below show that cholera toxin (CT), its B subunit (CTB), *E. coli* heat-labile enterotoxin (LT), and pertussis toxin are potent adjuvants for transcutaneous immunization, inducing high levels of IgG antibodies but not IgE antibodies. Also shown is that CTB without CT can also induce high levels of IgG antibodies. Thus, both bAREs and a derivative thereof can effectively immunize when epicutaneouly applied to the skin in a simple solution.

When an adjuvant such as CT is mixed with BSA, a protein not usually immunogenic when applied to the skin, anti-BSA antibodies are induced. An immune response to diphtheria toxoid was induced using pertussis toxin as adjuvant, but not with diphtheria toxoid alone. Thus, bAREs can act as adjuvants for non-immunogenic proteins in an transcutaneous immunization system.

Protection against the life-threatening infections diphtheria, pertussis, and tetanus (DPT) can be achieved by inducing high levels of circulating anti-toxin antibodies. Pertussis may be an exception in that some investigators feel that antibodies directed to other portions of the invading organism are necessary for protection, although this is controversial (see Schneerson et al., 1996) and most new generation acellular pertussis vaccines have PT as a component of the vaccine (Krueger and Barbieri, 1995). The pathologies in the diseases caused by DPT are directly related to the effects of their toxins and anti-toxin antibodies most certainly play a role in protection (Schneerson et al., 1996).

In general, toxins can be chemically inactivated to form toxoids which are less toxic but remain immunogenic. We envision that the transcutaneous immunization system using toxin-based immunogens and adjuvants can achieve anti-toxin levels adequate for protection against these diseases. The anti-toxin antibodies may be induced through immunization with the toxins, or genetically-detoxified toxoids themselves, or with toxoids and adjuvants such as CT. Genetically toxoided toxins which have altered ADP-ribosylating exotoxin activity, but not binding activity, are envisioned to be especially useful as non-toxic activators of antigen presenting cells used in transcutaneous immunization.

We envision that CT can also act as an adjuvant to induce antigen-specific CTLs through transcutaneous immunization (see Bowen et al., 1994; Porgador et al., 1997 for the use of CT as an adjuvant in oral immunization).

The bARE adjuvant may be chemically conjugated to other antigens including, for example, carbohydrates, polypeptides, glycolipids, and glycoprotein antigens. Chemical conjugation with toxins, their subunits, or toxoids with these antigens would be expected to enhance the immune response to these antigens when applied epicutaneously.

To overcome the problem of the toxicity of the toxins, (e.g., diphtheria toxin is known to be so toxic that one molecule can kill a cell) and to overcome the difficulty of working with such potent toxins as tetanus, several workers have taken a recombinant approach to producing genetically produced toxoids. This is based on inactivating the catalytic activity of the ADP-ribosyl transferase by genetic deletion. These toxins retain the binding capabilities, but lack the toxicity, of the natural toxins. This approach is described by Burnette et al. (1994), Rappuoli et al. (1995), and Rappuoli et al. (1996). Such genetically toxoided exotoxins could be useful for transcutaneous immunization system in that they would not create a safety concern as the toxoids would not be considered toxic. Additionally, several techniques exist to chemically toxoid toxins which can address the same problem (Schneerson et al., 1996). These techniques could be important for certain applications, especially pediatric applications, in which ingested toxins (e.g., diphtheria toxin) might possibly create adverse reactions.

Optionally, an activator of Langerhans cells may be used as an adjuvant. Examples of such activators include: inducers of heat shock protein; contact sensitizers (e.g., trinitrochlorobenzene, dinitrofluorobenzene, nitrogen mustard, pentadecylcatechol); toxins (e.g, Shiga toxin, Staph enterotoxin B); lipopolysaccharides, lipid A, or derivatives thereof; bacterial DNA (Stacey et al., 1996); cytokines (e.g., tumor necrosis factor-$\alpha$, interleukin-1$\beta$, -10, -12); and chemokines (e.g., defensins 1 or 2, RANTES, MIP-1$\alpha$, MIP-2, interleukin-8).

If an immunizing antigen has sufficient Langerhans cell activating capabilities then a separate adjuvant may not be required, as in the case of CT which is both antigen and adjuvant. It is envisioned that whole cell preparations, live viruses, attenuated viruses, DNA plasmids, and bacterial DNA could be sufficient to immunize transcutaneously. It may be possible to use low concentrations of contact sensitizers or other activators of Langerhans cells to induce an immune response without inducing skin lesions.

Liposomes and their Preparation

Liposomes are closed vesicles surrounding an internal aqueous space. The internal compartment is separated from the external medium by a lipid bilayer composed of discrete lipid molecules. In the present invention, antigen may be delivered through intact skin to specialized cells of the immune system, whereby an antigen-specific immune response is induced. Transcutaneous immunization may be achieved by using liposomes; however, as shown in the examples, liposomes are not required to elicit an antigen-specific immune response.

Liposomes may be prepared using a variety of techniques and membrane lipids (reviewed in Gregoriadis, 1993). Liposomes may be pre-formed and then mixed with antigen. The antigen may be dissolved or suspended, and then added to (a) the pre-formed liposomes in a lyophilized state, (b) dried lipids as a swelling solution or suspension, or (c) the solution of lipids used to form liposomes. They may also be formed from lipids extracted from the stratum corneum including, for example, ceramide and cholesterol derivatives (Wertz, 1992).

Chloroform is a preferred solvent for lipids, but it may deteriorate upon storage. Therefore, at one- to three-month intervals, chloroform is redistilled prior to its use as the solvent in forming liposomes. After distillation, 0.7% ethanol can be added as a preservative. Ethanol and methanol are other suitable solvents.

The lipid solution used to form liposomes is placed in a round-bottomed flask. Pear-shaped boiling flasks are preferred, particularly those flasks sold by Lurex Scientific (Vineland, N. J., cat. no. JM-5490). The volume of the flask should be more than ten times greater than the volume of the anticipated aqueous suspension of liposomes to allow for proper agitation during liposome formation.

Using a rotary evaporator, solvent is removed at 37° C. under negative pressure for 10 minutes with a filter aspirator attached to a water faucet. The flask is further dried under low vacuum (i.e., less than 50 mm Hg) for 1 hour in a dessicator.

To encapsulate antigen into liposomes, an aqueous solution containing antigen may be added to lyophilized liposome lipids in a volume that results in a concentration of approximately 200 mM with respect to liposome lipid, and shaken or vortexed until all the dried liposome lipids are wet. The liposome-antigen mixture may then be incubated for 18 hours to 72 hours at 4° C. The liposome-antigen formulation may be used immediately or stored for several years. It is preferred to employ such a formulation directly in the transcutaneous immunization system without removing unencapsulated antigen. Techniques such as bath sonication may be employed to decrease the size of liposomes, which may augment transcutaneous immunization.

Liposomes may be formed as described above but without addition of antigen to the aqueous solution. Antigen may then be added to the pre-formed liposomes and, therefore, antigen would be in solution and/or associated with, but not encapsulated by, the liposomes. This process of making a liposome-containing formulation is preferred because of its simplicity. Techniques such as bath sonication may be employed to alter the size and/or lamellarity of the liposomes to enhance immunization.

Although not required to practice the present invention, hydration and/or penetration of the stratum corneum may be enhanced by adding liposomes to the formulation. Liposomes have been used as carriers with adjuvants to enhance the immune response to antigens mixed with, encapsulated in, attached to, or associated with liposomes.

Transcutaneous Delivery of Antigen

Efficient immunization can be achieved with the present invention because transcutaneous delivery of antigen may target the Langerhans cell. These cells are found in abundance in the skin and are efficient antigen presenting cells leading to T-cell memory and potent immune responses (Udey, 1997). Because of the presence of large numbers of Langerhans cells in the skin, the efficiency of transcutaneous delivery may be related to the surface area exposed to antigen and adjuvant. In fact, the reason that transcutaneous immunization is so efficient may be that it targets a larger number of these efficient antigen presenting cells than intramuscular immunization.

We envision the present invention will enhance access to immunization, while inducing a potent immune response. Because transcutaneous immunization does not involve penetration of the skin and the complications and difficulties thereof, the requirements of trained personnel, sterile technique, and sterile equipment are reduced. Furthermore, the barriers to immunization at multiple sites or to multiple immunizations are diminished. Immunization by a single application of the formulation is also envisioned.

Immunization may be achieved using epicutaneous application of a simple solution of antigen and adjuvant impregnated in gauze under an occlusive patch, or by using other patch technologies; creams, immersion, ointments and sprays are other possible methods of application. The immunization could be given by untrained personnel, and is amenable to self-application. Large-scale field immunization could occur given the easy accessibility to immunization. Additionally, a simple immunization procedure would improve access to immunization by pediatric patients and the elderly, and populations in Third World countries.

For previous vaccines, their formulations were injected through the skin with needles. Injection of vaccines using needles carries certain drawbacks including the need for sterile needles and syringes, trained medical personnel to administer the vaccine, discomfort from the injection, and potential complications brought about by puncturing the skin with the needle. Immunization through the skin without the use of needles (i.e., transcutaneous immunization) represents a major advance for vaccine delivery by avoiding the aforementioned drawbacks.

The transcutaneous delivery system of the invention is also not concerned with penetration of intact skin by sound or electrical energy. Such a system that uses an electrical field to induce dielectric breakdown of the stratum corneum is disclosed in U.S. Pat. No. 5,464,386.

Moreover, transcutaneous immunization may be superior to immunization using needles as more immune cells would be targeted by the use of several locations targeting large surface areas of skin. A therapeutically effective amount of antigen sufficient to induce an immune response may be delivered transcutaneously either at a single cutaneous location, or over an area of intact skin covering multiple draining lymph node fields (e.g., cervical, axillary, inguinal, epitrochelear, popliteal, those of the abdomen and thorax). Such locations close to numerous different lymphatic nodes at locations all over the body will provide a more widespread stimulus to the immune system than when a small amount of antigen is injected at a single location by intradermal subcutaneous or intramuscular injection.

Antigen passing through or into the skin may encounter antigen presenting cells which process the antigen in a way that induces an immune response. Multiple immunization sites may recruit a greater number of antigen presenting cells and the larger population of antigen presenting cells that were recruited would result in greater induction of the immune response. It is conceivable that absorption through the skin may deliver antigen to phagocytic cells of the skin such as, for example, dermal dendritic cells, macrophages, and other skin antigen presenting cells; antigen may also be delivered to phagocytic cells of the liver, spleen, and bone marrow that are known to serve as the antigen presenting cells through the blood stream or lymphatic system. The result would be widespread distribution of antigen to antigen presenting cells to a degree that is rarely, if ever achieved, by current immunization practices.

The transcutaneous immunization system may be applied directly to the skin and allowed to air dry; rubbed into the skin or scalp; held in place with a dressing, patch, or absorbent material; otherwise held by a device such as a stocking, slipper, glove, or shirt; or sprayed onto the skin to maximize contact with the skin. The formulation may be applied in an absorbant dressing or gauze. The formulation may be covered with an occlusive dressing such as, for example, AQUAPHOR (an emulsion of petrolatum, mineral oil, mineral wax, wool wax, panthenol, bisabol, and glycerin from Beiersdorf, Inc.), plastic film, COMFEEL (Coloplast) or vaseline; or a non-occlusive dressing such as, for example, DUODERM (3M) or OPSITE (Smith & Napheu). An occlusive dressing completely excludes the passage of water.

The formulation may be applied to single or multiple sites, to single or multiple limbs, or to large surface areas of the skin by complete immersion. The formulation may be applied directly to the skin.

Genetic immunization has been described in U.S. Pat. Nos. 5,589,466 and 5,593,972. The nucleic acid(s) contained in the formulation may encode the antigen, the adjuvant, or both. The nucleic acid may or may not be capable of replication; it may be non-integrating and non-infectious. The nucleic acid may further comprise a regulatory region (e.g., promoter, enhancer, silencer, transcription initiation and termination sites, RNA splice acceptor and donor sites, polyadenylation signal, internal ribosome binding site, translation initiation and termination sites) operably linked to the sequence encoding the antigen or adjuvant. The nucleic acid may be complexed with an agent that promotes transfection such as cationic lipid, calcium phosphate, DEAE-dextran, polybrene-DMSO, or a combination thereof. The nucleic acid may comprise regions derived from viral genomes. Such materials and techniques are described by Kriegler (1990) and Murray (1991).

An immune response may comprise humoral (i.e., antigen-specific antibody) and/or cellular (i.e., antigen-specific lymphocytes such as B cells, $CD4^+$ T cells, $CD8^+$ T cells, CTL, Th1 cells, Th2 cells, and/or $T_{DTH}$ cells) effector arms. Moreover, the immune response may comprise NK cells that mediate antibody-dependent cell-mediated cytotoxicity (ADCC).

The immune response induced by the formulation of the invention may include the elicitation of antigen-specific antibodies and/or cytotoxic lymphocytes (CTL, reviewed in Alving and Wassef, 1994). Antibody can be detected by immunoassay techniques, and the detection of various isotypes (e.g., IgM, IgD, IgA1, IgA2, secretory IgA, IgE, IgG1, IgG2, IgG3, or IgG4) may be expected. An immune response can also be detected by a neutralizing assay.

Antibodies are protective proteins produced by B lymphocytes. They are highly specific, generally targeting one epitope of an antigen. Often, antibodies play a role in protection against disease by specifically reacting with antigens derived from the pathogens causing the disease. Immunization may induce antibodies specific for the immunizing antigen, such as cholera toxin. These antigen-specific antibodies are induced when antigen is delivered through the skin by liposomes.

CTLs are particular protective immune cells produced to protect against infection by a pathogen. They are also highly specific. Immunization may induce CTLs specific for the antigen, such as a synthetic oligopeptide based on a malaria protein, in association with self-major histocompatibility antigen. CTLs induced by immunization with the transcutaneous delivery system may kill pathogen infected cells. Immunization may also produce a memory response as indicated by boosting responses in antibodies and CTLs, lymphocyte proliferation by culture of lymphocytes stimulated with the antigen, and delayed type hypersensitivity responses to intradermal skin challenge of the antigen alone.

In a viral neutralization assay, serial dilutions of sera are added to host cells which are then observed for infection after challenge with infectious virus. Alternatively, serial dilutions of sera may be incubated with infectious titers of virus prior to innoculation of an animal, and the innoculated animals are then observed for signs of infection.

The transcutaneous immunization system of the invention may be evaluated using challenge models in either animals or humans, which evaluate the ability of immunization with the antigen to protect the subject from disease. Such protection would demonstrate an antigen-specific immune response. In lieu of challenge, achieving anti-diphtheria antibody titers of 5 IU/ml or greater is generally assumed to indicate optimum protection and serves as a surrogate marker for protection (Plotkin and Mortimer, 1994).

Furthermore, the *Plasmodium faciparum* challenge model may be used as to induce an antigen-specific immune response in humans. Human volunteers may be immunized using the transcutaneous immunization system containing oligopeptides or proteins (polypeptides) derived from the malaria parasite, and then exposed to malaria experimentally or in the natural setting. The *Plasmodium yoelii* mouse malaria challenge model may be used to evaluate protection in the mouse against malaria (Wang et al., 1995).

Alving et al. (1986) injected liposomes comprising lipid A as an adjuvant for inducing an immune response to cholera toxin (CT) in rabbits and to a synthetic protein consisting of a malaria oligopeptide containing four tetra-peptides (Asn-Ala-Asn-Pro) conjugated to BSA. The authors found that the immune response to cholera toxin or to the synthetic malaria protein was markedly enhanced by encapsulating the antigen within the liposomes containing lipid A, compared to similar liposomes lacking lipid A. Several antigens derived either from the circumsporozoite protein (CSP) or from merozoite surface proteins of *Plasmodium falciparum* have been encapsulated in liposomes containing lipid A. All of the malaria antigens that have been encapsulated in liposomes containing lipid A have been shown to induce humoral effectors (i.e., antigen-specific antibodies), and some have been shown to induce cell-mediated responses as well. Generation of an immune response and immunoprotection in an animal vaccinated with a malaria antigen may be assayed by immunofluorescence to whole, fixed malaria sporozoites or CTLs killing of target cells transfected with CSP.

Mice may be transcutaneously immunized with cholera toxin, and then challenged intranasally with an $LD_{70}$ (40 $\mu$g) dose of cholera toxin and observed for protection. Mallet et al. (personal communication) have found that C57BL/6 mice develop a fatal hemorrhagic pneumonia in response to intranasal challenge with CT. Alternatively, the mice may be challenged with an intraperitoneal dose of CT (Dragunsky et al., 1992). Cholera toxin-specific IgG or IgA antibody may provide protection against cholera toxin challenge (Pierce, 1978; Pierce and Reynolds, 1974).

Vaccination has also been used as a treatment for cancer and autoimmune disease. For example, vaccination with a tumor antigen (e.g., prostate specific antigen) may induce an immune response in the form of antibodies, CTLs and lymphocyte proliferation which allows the body's immune system to recognize and kill tumor cells. Tumor antigens useful for vaccination have been described for melanoma (U.S. Pat. Nos. 5,102,663, 5,141,742, and 5,262,177), prostate carcinoma (U.S. Pat. No. 5,538,866), and lymphoma (U.S. Pat. Nos. 4,816,249, 5,068,177, and 5,227,159). Vaccination with T-cell receptor oligopeptide may induce an immune response that halts progression of autoimmune disease (U.S. Pat. Nos. 5,612,035 and 5,614,192; Antel et al., 1996; Vandenbark et al., 1996). U.S. Pat. No. 5,552,300 also describes antigens suitable for treating autoimmune disease.

The following is meant to be illustrative of the present invention; however, the practice of the invention is not limited or restricted in any way by the examples.

EXAMPLES

Immunization Procedure

BALB/c mice of 6 to 8 weeks were shaved with a #40 clipper. This shaving could be done without any signs of trauma to the skin. The shaving was done from the mid-thorax to just below the nape of the neck. The mice were then allowed to rest for 24 hours. Prior to this the mice had been ear-tagged for identification, and pre-bled to obtain a sample of pre-immune serum. Mice were also transcutaneously immunized without shaving by applying 50 $\mu$l of immunizing solution to each ear.

The mice were then immunized in the following way. Mice were anesthetized with 0.03–0.06 ml of a 20 mg/ml solution of xylazine and 0.5 ml of 100 mg/ml ketamine; mice were immobilized by this dose of anesthesia for approximately one hour. The mice were placed ventral side down on a warming blanket.

The immunizing solution was then placed on the dorsal shaved skin of a mouse in the following manner: a 1.2 cm×1.6 cm stencil made of polystyrene was laid gently on the back and a saline-wetted sterile gauze was used to partially wet the skin (this allowed even application of the immunizing solution), the immunizing solution was then applied with a pipet to the area circumscribed by the stencil to yield a 2 $cm^2$ patch of immunizing solution. Care was used not to scrape or rub the skin with the pipet tip. The immunizing solution was spread around the area to be covered with the smooth side of the pipet tip.

The immunizing solution (between about 100 $\mu$l to about 200 $\mu$l) was left on the back of the mouse for 60 minutes. At the end of 60 minutes, the mouse was held gently by the nape of the neck and the tail under a copious stream of lukewarm tap water, and washed for 10 seconds. The mouse was then gently patted dry with a piece of sterile gauze and a second washing was performed for 10 seconds; the mouse was then patted dry a second time and left in the cage. The mice appeared to exhibit no adverse effects from the anesthesia, immunization, washing procedure, or toxicity from the exotoxins. No skin irritation, swelling or redness was seen after the immunization and the mice appeared to thrive. Immunization using the ear was performed as described above except that fur was not removed prior to immunization.

Antigen

The following antigens were used for immunization and ELISA, and were mixed using sterile PBS or normal saline. Cholera toxin or CT (List Biologicals, Cat #101B, lot #10149CB), CT B subunit (List Biologicals, Cat #BT01, lot #CVXG-14E), CT A subunit (List Biologicals, Cat #102A, lot #CVXA-17B), CT A subunit (Calbiochem, Cat #608562); pertussis toxin, salt-free (List Biologicals, lot #181120a); tetanus toxoid (List Biologicals, lots #1913a and #1915a); Pseudomonas exotoxin A (List Biologicals, lot #ETA25a); diphtheria toxoid (List Biologicals, lot #15151); heat-labile enterotoxin from *E. coli* (Sigma, lot #9640625); bovine serum albumin or BSA (Sigma, Cat #3A-4503, lot #31F-0116); and Hemophilus influenza B conjugate (Connaught, lot #6J81401). ELISA-IgG(H+L)

Antibodies specific for CT, LT, ETA, pertussis toxin, diphtheria toxoid, tetanus toxoid, Hemophilus influenza B conjugate, and BSA were determined using ELISA in a technique similar to Glenn et al. (1995). All antigens were dissolved in sterile saline at a concentration of 2 $\mu$g/ml. Fifty microliters of this solution (0.1 $\mu$g) per well was put on IMMULON-2 polystyrene plates (Dynatech Laboratories, Chantilly, Va.) and incubated at room temperature overnight. The plates were then blocked with a 0.5% casein/0.05% Tween 20 blocking buffer solution for one hour. Sera was diluted with 0.5% casein/0.05% Tween 20 diluent; dilution series were done in columns on the plate. Incubation was for 2 hours at room temperature.

The plates were then washed in a PBS-0.05% Tween 20 wash solution four times, and goat anti-mouse IgG(H+L) horseradish peroxidase (HRP)-linked (Bio-Rad Laboratories, Richmond, Calif., Cat #170-6516) secondary antibody was diluted in casein diluent at a dilution of 1/500 and left on the plates for one hour at room temperature. The plates were then washed four times in the PBS-Tween wash solution. One hundred microliters of 2,2'-azino-di(3-ethyl-benzthiazolone)sulphonic acid substrate (Kirkegaard and Perry) were added to each well and the plates were read at 405 nm after 20–40 minutes of development. Results are reported as the geometric mean of individual sera and standard error of the mean of ELISA units (the serum dilution at which the absorbance in equal to 1.0) or as individual antibody responses in ELISA units. ELISA-IgG ($\gamma$), IgM($\mu$) and IgA($\alpha$)

IgG($\gamma$), IgM($\mu$) and IgA($\alpha$) anti-CT antibody levels were determined using ELISA with a technique similar to Glenn et al. (1995). CT was dissolved in sterile saline at a concentration of 2 $\mu$g/ml. Fifty microliters of this solution (0.1 $\mu$g) per well were put on IMMULON-2 polystyrene plates (Dynatech Laboratories, Chantilly, Va.) and incubated at room temperature overnight. The plates were then blocked with a 0.5% casein-Tween 20 blocking buffer solution for one hour. Sera was diluted and casein diluent and serial dilutions were done on the plate. This was incubated for two hours at room temperature.

The plates were then washed in a PBS-Tween wash solution four times and goat anti-mouse IgG($\gamma$) HRP-linked (Bio-Rad Laboratories, Richmond, Calif., Cat #172-1038), goat anti-mouse IgM($\mu$) HRP-linked (BioRad Laboratories, Richmond, Calif., Cat #172-1030), or goat anti-mouse IgA HRP-linked (Sigma, St. Louis, Mo., Cat #1158985) secondary antibody was diluted in casein diluent in a dilution of 1/1000 and left on the plates for one hour at room temperature. The plates were then washed four times in a PBS-Tween wash solution. One hundred microliters of 2,2'-azino-di(3-ethyl benzthiazolone)sulphonic acid substrate from (Kirkegaard and Perry, Gaithersburg, Md.) were added to the wells and the plates were read at 405 nm. Results are reported as the geometric mean of individual sera and standard error of the mean of ELISA units (the serum dilution at which the absorbance in equal to 1.0).

ELISA-IgG Subclass

Antigen-specific IgG (IgG1, IgG2a, IgG2b, and IgG3) subclass antibody against CT, LT, ETA, and BSA was performed as described by Glenn et al. (1995). The solid phase ELISA was performed in IMMULON-2 polystyrene plates (Dynatech Laboratories, Chantilly, Va.). Wells were incubated with the respective antigens in saline overnight (0.1 $\mu$g/50 $\mu$l) and blocked with 0.5% casein-Tween 20. Individual mouse sera diluted in 0.5% casein were serially diluted, and incubated at room temperature for four hours. Secondary antibody consisted of horseradish peroxidase-conjugated goat anti-mouse isotype-specific antibody (IgG1, IgG2a, IgG2b, IgG3, The Binding Site, San Diego, Calif.). A standard curve for each subclass was determined using mouse myeloma IgG1, IgG2a, IgG2b, and IgG3 (The Binding Site, San Diego, Calif.). Standard wells were coated with goat anti-mouse IgG(H+L) (Bio-Rad Laboratories, Richmond, Calif., Cat #172-1054) to capture the myeloma IgG subclass standards which were added in serial dilutions. The myeloma IgG subclass was also detected using the peroxidase-conjugated goat anti-mouse subclass-specific antibody. Both the test sera and myeloma standards were detected using 2,2'-azino-di(3-ethyl-benzthiazolone) sulphonic acid (Kirkegaard and Perry, Gaithersburg, Md.) as substrate. Absorbances were read at 405 nm. Individual antigen specific subclasses were quantitated using the values from the linear titration curve computed against the myeloma standard curve and reported as $\mu$g/ml.

ELISA-IgE

Antigen-specific IgE antibody quantitation was performed using a protocol from Pharmingen Technical Protocols, page 541 of the Research Products Catalog, 1996-1997 (Pharmingen, San Diego, Calif.). Fifty microliters of 2 $\mu$g/ml purified anti-mouse IgE capture mAb (Pharmingen, Cat #02111D) in 0.1 M NaHCO$_3$ (pH 8.2) were added to IMMUNO plates (Nunc, Cat #12-565-136). Plates were incubated overnight at room temperature, washed three times with PBS-Tween 20, blocked with 3% BSA in PBS for two hours, and washed three times with PBS-Tween. Sera were diluted in 1% BSA in PBS, added at dilutions of 1/100, and diluted serially down the columns (e.g., 1/100, 1/200, et cetera). Purified mouse IgE standards (Pharmingen, Cat #0312D) were added with a starting dilution of 0.25 $\mu$g/ml and serially diluted down the columns. Plates were incubated for two hours and washed five times with PBS-Tween.

Biotinylated anti-mouse IgE mAB (Pharmingen, Cat #02122D) to 2 $\mu$g/ml in 1% BSA in PBS, incubated for 45 minutes and washed five times with PBS-Tween. Avidin-peroxidase (Sigma A3151, 1:400 of 1 mg/ml solution) was added for 30 min and plates were washed six times with PBS-Tween. Both the test sera and IgE standards were detected using 2,2'-azino-di(3ethyl-benzthiazolone) sulphonic acid (Kirkegaard and Perry, Gaithersburg, Md.) as substrate. Absorbances were read at 405 nm. Individual antigen specific subclasses were quantitated using the values from the linear titration curve computed against the IgE standard curve and reported as $\mu$g/ml.

Liposome Preparation

Where liposomes were included in the formulation for transcutaneous immunization, multilamellar liposomes composed of dimyristoyl phosphatidyl choline, dimyristoyl phosphatidyl glycerol, cholesterol were prepared according to Alving et al. (1993). Dimyristoyl phosphatidylcholine, dimyristoyl phosphatidylglycerol, and cholesterol were purchased from Avanti Polar Lipids Inc. (Alabaster, Ala.). Stock solutions of the lipids in chloroform were removed from −20° C. freezer where they were stored.

The lipids were mixed in a molar ratio of 0.9:0.1:0.75 dimyristoyl phosphatidyl choline, dimyristoyl phosphatidyl glycerol, and cholesterol in a pear shaped flask. Using a rotary evaporator, the solvent was removed at 37° C. under negative pressure for 10 minutes. The flask was further dried under low vacuum for two hours in a dessicator to remove residual solvent. The liposomes were swollen at 37 mM phospholipid using sterile water, lyophilized and stored at −20° C. These liposomes were mixed in their lyophilized state with normal saline (pH 7.0) to achieve a designated phospholipid concentration in the saline. Alternatively, the dried lipids were swollen to make liposomes with normal saline (pH 7.0) and were not lyophilized.

Example 1

BALB/c mice at 6 to 8 weeks of age were immunized transcutaneously as described above for "Immunization Procedure", in groups of five mice. The mice were immunized using 100 μl of immunization solution which was prepared as follows: liposomes prepared as described above for "Liposome Preparation" were mixed with saline to form the liposomes. The pre-formed liposomes were then diluted in either saline (liposome alone group) or with CT in saline to yield an immunizing solution containing liposomes at 10–150 mM phospholipid with 100 μg of CT per 100 μl of immunizing solution. CT was mixed in saline to make an immunizing solution containing 100 μg of CT per 100 μg of solution for the group receiving CT alone. Solutions were vortexed for 10 seconds prior to immunization.

The mice were immunized transcutaneously at 0 and 3 weeks. Antibody levels were determined using ELISA as described above for "ELISA IgG(H+L)" 3 weeks after the boosting immunization, and compared against pre-immune sera. As shown in Table 1, the level of anti-CT antibodies induced by CT without liposomes was not different from the level of anti-CT antibodies generated using liposomes except in the mice where 150 mM liposomes were used. CT in saline alone was able to immunize mice against CT to produce high antibody titers.

Table 1

| Anti-CT antibodies | | |
|---|---|---|
| Group | ELISA Units | SEM |
| CT alone | 27,482 | (16,635–48,051) |
| CT + 150 mM Liposomes | 4,064 | *(2,845–5,072) |
| CT + 100 mM Liposomes | 35,055 | (25,932–44,269) |
| CT + 50 mM Liposomes | 9,168 | (4,283–12,395) |
| CT + 25 mM Liposomes | 18,855 | (12,294–40,374) |
| CT + 10 mM Liposomes | 28,660 | (18,208–31,498) |
| 50 mM Liposomes | 0 | |

*Significantly different from the Group CT alone (P < 0.05)

Example 2

BALB/c mice at 6 to 8 weeks of age were immunized transcutaneously as described above for "Immunization Procedure", in groups of five mice. The mice were immunized at 0 and 3 weeks using 100 μl of immunization solution prepared as follows: BSA was mixed in saline to make an immunizing solution containing 200 μg of BSA per 100 μl of saline for the group receiving BSA alone; BSA and CT were mixed in saline to make an immunizing solution containing 200 μg of BSA and 100 μg of CT per 100 μl of saline for the group receiving BSA and CT. Where liposomes were used, the liposomes were prepared as described above for "Liposome Preparation", and were first mixed with saline to form the liposomes. They were then diluted in BSA or BSA and CT in saline to yield an immunizing solution containing liposomes at 50 mM phospholipid with 200 μg of BSA per 100 μl of immunizing solution, or 200 μg BSA+100 μg CT per 100 μl of immunizing solution. Solutions were vortexed for 10 seconds prior to immunization.

The antibodies were determined using ELISA as described above for "ELISA IgG(H+L)" on sera 3 weeks after the second immunization. The results are shown in Table 2. BSA alone, with or without liposomes, was not able to elicit an antibody response. However, the addition of CT stimulated an immune response to BSA. CT acted as a adjuvant for the immune response to BSA, and anti-BSA antibodies of high titer were produced.

TABLE 2

| Anti-BSA antibodies | | |
|---|---|---|
| Group | ELISA Units | SEM |
| BSA in saline | 0 | |
| BSA + 50 mM Liposomes | 0 | |
| CT + BSA in saline | 8,198 | (5,533–11,932) |
| CT + BSA + 50 mM | 3,244 | (128–3,242) |

Example 3

BALB/c mice at 6 to 8 weeks of age were immunized transcutaneously as described above for "Immunization Procedure", in groups of five mice. The mice were immunized at 0 and 3 weeks using 100 μl of immunization solution prepared as follows: LT was mixed in saline to make an immunizing solution containing 100 μg of LT per 100 μl of saline for the group receiving LT alone. Where liposomes were used the liposomes prepared as described above for "Liposome Preparation", and were first mixed with saline to form the liposomes. The pre-formed liposomes were then diluted in LT in saline to yield an immunizing solution containing liposomes at 50 mM phospholipid with 100 μg of LT per 100 μl of immunizing solution. Solutions were vortexed for 10 seconds prior to immunization.

The anti-LT antibodies were determined using ELISA as described above for "ELISA IgG(H+L)" 3 weeks after the second immunization. The results are shown in Table 3. LT was clearly immunogenic both with and without liposomes, and no significant difference between the groups could be detected. LT and CT are members of the family of bacterial ADP-ribosylating exotoxins (bAREs). They are organized as A:B proenzymes with the ADP-ribosyltransferase activity contained in the A subunit and the target cell binding a function of the B subunit. LT is 80% homologous with CT at the amino acid level and has a similar non-covalently bound subunit organization, stoichiometry (A:B5), the same binding target, ganglioside GM1, and is similar in size (MW ~80,000). The similarities of LT and CT appear to influence their immunogenicity by the transcutaneous route as reflected by the similar magnitude of the antibody response to both CT and LT (Tables 1 and 3).

TABLE 3

| Anti-LT antibodies | | |
|---|---|---|
| Group | ELISA Units | SEM |
| LT in saline | 23,461 | (20,262–27,167) |
| LT + 50 mM Liposomes | 27,247 | (19,430–38,211) |

Example 4

C57BL/6 mice at 6 to 8 weeks of age were immunized transcutaneously as described above for "Immunization Procedure", in groups of five mice. The mice were immunized once using 100 μl of immunization solution prepared as follows: LT was mixed in saline to make an immunizing solution containing 100 μg of LT per 100 μl of saline. The solution was vortexed for 10 seconds prior to immunization.

The anti-LT antibodies were determined using ELISA as described above for "ELISA IgG(H+L)" 3 weeks after the single immunization. The results are shown in Table 4. LT was clearly immunogenic with a single immunization and antibodies were produced by 3 weeks. Rapid enhancement of antibody titers and responses to single immunization would be a useful aspect of the transcutaneous immunization method. It is conceivable that a rapid single immunization would be useful in epidemics, for travelers, and where access to medical care is poor.

TABLE 4

Anti-LT antibodies

| Mouse Number | ELISA Units |
|---|---|
| 5141 | 6,582 |
| 5142 | 198 |
| 5143 | 229 |
| 5144 | 6,115 |
| 5145 | 17,542 |
| Geo Mean | 2,000 |

Example 5

C57BL6 mice at 8 to 12 weeks of age were immunized transcutaneously as described above for "Immunization Procedure", in groups of five mice. The mice were immunized once using 100 μl of immunization solution prepared as follows: CT was mixed in saline to make an immunizing solution containing 100 μg of CT per 100 μl of saline. The solution was vortexed for 10 seconds prior to immunization.

The anti-CT antibodies were determined using ELISA as described above for "ELISA IgG(H+L)" 3 weeks after the single immunization. The results are shown in Table 5. CT was highly immunogenic with a single immunization. Rapid enhancement of antibody titers and responses to single immunication may be a useful aspect of the transcutaeous immunization method. It is conceivable that a rapid single immunization would be useful in epidemics, for travelers, and where access to medical care is poor.

TABLE 5

Anti-CT antibodies

| Mouse Number | ELISA Units |
|---|---|
| 2932 | 18,310 |
| 2933 | 30,878 |
| 2934 | 48,691 |
| 2935 | 7,824 |
| Geo Mean | 21,543 |

Example 6

BALB/c mice at 6 to 8 weeks of age were immunized transcutaneously as described above for "Immunization Procedure", in groups of five mice. The mice were immunized at 0 and 3 weeks using 100 μl of immunization solution prepared as follows: ETA was mixed in saline to make an immunizing solution containing 100 μg of ETA per 100 μl of saline for the group receiving ETA alone. Where liposomes were used, the liposomes were prepared as described above for "Liposome Preparation", and were first mixed with saline to form the liposomes. The pre-formed liposomes were then diluted with ETA in saline to yield an immunizing solution containing liposomes at 50 mM phospholipid with 100 μg of ETA per 100 μl of immunizing solution. Solutions were vortexed for 10 seconds prior to immunization.

The antibodies were determined using ELISA as described above for "ELISA IgG(H+L)" on sera 3 weeks after the second immunization. The results are shown in Table 6. ETA was clearly immunogenic both with and without liposomes, and no significant difference between the groups could be detected. ETA differs from CT and LT in that ETA is a single 613 amino acid peptide with A and B domains on the same peptide and binds to an entirely different receptor, the α2-macroglobulin receptor/low density lipoprotein receptor-related protein (Kounnas et al., 1992). Despite the dissimilarities between ETA and CT in size, structure, and binding target, ETA also induced a transcutaneous antibody response.

TABLE 6

Anti-ETA antibodies

| Group | ELISA Units | SEM |
|---|---|---|
| ETA in saline | 3,756 | (1,926–7,326) |
| ETA + 50 mM Liposomes | 857 | (588–1,251) |

Example 7

BALB/c mice at 6 to 8 weeks of age were immunized transcutaneously as described above for "Immunization Procedure", in groups of five mice. The mice were immunized using 100 μl of immunization solution which was prepared as follows: CT was mixed in saline to make 100 μg of CT per 100 μl of immunizing solution, LT was mixed in saline to make 100 μg of LT per 100 μl of immunizing solution, ETA was mixed in saline to make 100 μg of ETA per 100 μl of immunizing solution, and CT and BSA were mixed in saline to make 100 μg of CT per 100 μl of immunizing solution and 200 μg of BSA per 100 μl of immunizing solution. Solutions were vortexed for 10 seconds prior to immunization.

The mice were immunized transcutaneously at 0 and 3 weeks and the antibody levels were determined using ELISA as described above for "ELISA IgG Subclass", three weeks after the boosting immunization and compared against the pre-immune sera. The IgG subclass response to CT, BSA and LT had similar levels of IgG1 and IgG2a reflecting activation of T help from both Th1 and Th2 lymphocytes (Seder and Paul, 1994), whereas the IgG subclass response to ETA consisted of almost exclusively IgG1 and IgG3, consistent with a Th2-like response (Table 7). Thus, it appears that all IgG subclasses can be produced using transcutaneous immunization.

TABLE 7

IgG subclasses of induced antibodies

| Imm. Antigen | Antibody Specificity | IgG1 (μg/μl) | IgG2a (μg/μl) | IgG2b (μg/μl) | IgG3 (μg/μl) |
|---|---|---|---|---|---|
| CT | CT | 134 | 25 | 27 | 0 |
| CT + BSA | BSA | 108 | 17 | 12 | 5 |
| LT | LT | 155 | 28 | 10 | 8 |
| ETA | ETA | 50 | 0 | 1 | 10 |

Example 8

BALB/c mice at 6 to 8 weeks of age were immunized transcutaneously as described above for "Immunization Procedure", in groups of five mice. The mice were immunized using 100 μl of immunization solution which was prepared as follows: LT was mixed in saline to make an immunizing solution containing 100 μg of LT per 100 μl of saline for the group receiving LT alone, CT was mixed in saline to make an immunizing solution containing 100 μg of CT per 100 μl of saline for the group receiving CT alone, ETA was mixed in saline to make an immunizing solution containing 100 μg of ETA per 100 μl of saline for the group receiving ETA alone, and BSA and CT were mixed in saline to make an immunizing solution containing 100 μg of BSA and 100 μg of CT per 100 μl of saline for the group receiving BSA and CT.

The mice were immunized transcutaneously at 0 and 3 weeks and the antibody levels were determined using ELISA as described above for "ELISA IgE", one week after the boosting immunization and compared against the pre-immune sera. As shown in Table 8, no IgE antibodies were found although the sensitivity of detection was 0.003 μg/ml. IgG antibodies were determined in the same mice using "ELISA IgG(H+L)" on sera 3 weeks after the second immunization. The IgG antibody response to LT, ETA, CT and BSA are shown to indicate that the animals were successfully immunized and responded with high titers of antibodies to the respective antigens.

TABLE 8

IgE antibodies to LT, ETA, CT and BSA

| Group | Antibody Specificity | IgE (μg/ml) | IgG (ELISA Units) |
| --- | --- | --- | --- |
| LT | Anti-LT | 0 | 23,461 |
| ETA | Anti-ETA | 0 | 3,756 |
| CT | Anti-CT | 0 | 39,828 |
| CT + BSA | Anti-BSA | 0 | 8,198 |

Example 9

BALB/c mice at 6 to 8 weeks of age immunized transcutaneously as described above for "Immunization Procedure", in groups of five mice. The mice were immunized at 0 and 3 weeks using 100 ml of immunization solution which was prepared as follows: CT was mixed in saline to make an immunizing solution containing 100 mg of CT per 100 ml of immunizing solution. The immunization solution was vortexed for 10 seconds prior to immunization.

The mice were immunized transcutaneously at 0 and 3 weeks and the antibody levels were determined using ELISA as described above for "ELISA IgG(H+L)" and "ELISA IgG(γ)". Determinations were done at 1 and 4 weeks after the initial immunization, and compared against the pre-immune sera. As shown in Table 9, high levels of anti-CT IgG(γ) antibodies were induced by CT in saline. Small amounts of IgM could be detected by using IgM(μ) specific secondary antibody. By 4 weeks, the antibody response was primarily IgG. Data are reported in ELISA units.

TABLE 9

IgE (γ) and IgM (μ)

| Imm. Group | Week | IgG (γ) | IgM (μ) |
| --- | --- | --- | --- |
| CT | 1 | 72 | 168 |
| CT | 4 | 21,336 | 38 |
| L() + CT | 1 | 33 | 38 |
| L() + CT | 4 | 22,239 | 70 |

Example 10

BALB/c mice at 6 to 8 weeks of age were immunized transcutaneously as described above for "Immunization Procedure", in groups of five mice. The mice were immunized once using 100 μl of immunization solution prepared as follows: CT was mixed in saline to make an immunizing solution containing 100 μg of CT per 100 μl of saline. The solution was vortexed for 10 seconds prior to immunization. The mice were immunized transcutaneously at 0 and 3 weeks. Antibody levels were determined using ELISA as described above for "ELISA IgG(H+L)" 5 weeks after the boosting immunization, and compared against pre-immune sera. As shown in Table 10, serum anti-CT IgA antibodies were detected.

TABLE 10

Anti-CT IgA antibodies

| Mouse Number | IgA (ng/ml) |
| --- | --- |
| 1501 | 232 |
| 1502 | 22 |
| 1503 | 41 |
| 1504 | 16 |
| 1505 | 17 |

Example 11

BALB/c mice at 6 to 8 weeks of age were immunized transcutaneously as described above for "Immunization Procedure", in groups of five mice. The mice were immunized using 100 μl of immunization solution which was prepared as follows: CT was mixed in saline to make an immunizing solution containing 100 μg of CT per 100 μl of immunizing solution. The immunization solution was vortexed for 10 seconds prior to immunization.

The mice were immunized with 100 μl of immunizing solution transcutaneously at 0 and 3 weeks and the antibody levels were determined using ELISA as described above for "ELISA IgG(H+L)" and "ELISA IgG(γ)". Antibody determinations were done at 8 weeks after the initial immunization and compared against the pre-immune sera. As shown in Table 11, high levels of serun anti-CT antibodies were induced by CT in saline. Lung wash IgG could be detected by ELISA using IgG(H+L) or IgG(γ) specific antibody. The antibody found on the lung mucosal surface is diluted by the lavage method used to collect mucosal antibody and, thus, the exact amounts of antibody detected are not as significant as the mere presence of detectable antibody.

Lung washes were obtained after sacrificing the mouse. The trachea and lungs were exposed by gentle dissection and trachea was transected above the bifurcation. A 22 gauge polypropylene tube was inserted and tied off on the trachea to form a tight seal at the edges. Half a milliliter of PBS was infused using a 1 ml syringe attached to the tubing and the lungs were gently inflated with the fluid. The fluid was withdrawn and reinfused for a total of 3 rounds of lavage. The lung wash was then frozen at −20° C.

Table 11 shows the IgG(H+L) and IgG(γ) antibody response to cholera toxin in the sera and lung washes at 8 weeks. Data are expressed in ELISA units. Antibodies were clearly detectable for all mice in the lung washes. The presence of antibodies in the mucosa may be important for protection against mucosally active diseases.

TABLE 11

Mucosal Antibody to CT

| Animal # | Imm. Group | IgG (H + L) | IgG(γ) | Source |
|---|---|---|---|---|
| 1501 | CT | 133 | 34 | Lungs |
| 1502 | CT | 75 | 12 | Lungs |
| 1503 | CT | 162 | 28 | Lungs |
| 1504 | CT | 144 | 18 | Lungs |
| 1505 | CT | 392 | 56 | Lungs |
|  | Geo Mean | 156 | 26 |  |
| 1501 | CT | 34,131 | 13,760 | Sera |
| 1502 | CT | 11,131 | 2,928 | Sera |
| 1503 | CT | 21,898 | 10,301 | Sera |
| 1504 | CT | 22,025 | 8,876 | Sera |
| 1505 | CT | 34,284 | 10,966 | Sera |
|  | Geo Mean | 23,128 | 8,270 |  |

Example 12

BALB/c mice were immunized transcutaneously at 0 and 3 weeks as described above for "Immunization Procedure", in groups of four mice. Liposomes were prepared as described above for "Liposome Preparation", and were first mixed with saline to form the liposomes. The pre-formed liposomes were then diluted with either CT, CTA or CTB in saline to yield an immunizing solution containing liposomes at 50 mM phospholipid with 50 μg of antigen (CT, CTA or CTB) per 100 μl of immunizing solution. Solutions were vortexed for 10 seconds prior to immunization.

The antibodies were determined using ELISA as described above for "ELISA IgG(H+L)", one week after the boosting immunization and compared against the pre-immune sera. The results are shown in Table 12. CT and CTB were clearly immunogenic whereas CTA was not. Thus, the B subunit of CT is necessary and sufficient to induce a strong antibody response.

TABLE 12

Antibodies to CT, CTA and CTB

| Group | Anti-CT | Anti-CTA | Anti-CTB |
|---|---|---|---|
| CT + 50 mM Liposomes | 12,636 | 136 | 7,480 |
| CTB + 50 mM Liposomes | 757 | 20 | 1,986 |
| CTA + 50 mM Liposomes | 0 | 0 | 0 |

Example 13

BALB/c mice were immunized transcutaneously as described above for "Immunization Procedure", in groups of five mice. Mice were immunized at 0 and 3 weeks with 100 μg of diphtheria toxoid and 10 μg of pertussis toxin per 100 μl of saline solution. Solutions were vortexed for 10 seconds prior to immunization.

The antibodies were quantitated using ELISA as described for "ELISA IgG(H+L)". Anti-diphtheria toxoid antibodies were detected only in animals immunized with both pertussis toxin and diphtheria toxoid. The highest responder had anti-diphtheria toxoid antibody ELISA units of 1,038. Thus, a small amount of pertussis toxin acts as an adjuvant for diphtheria toxoid antigen. The toxoid alone did not induce an immune response suggesting that the toxoiding process has affected the portion of the molecule responsible for the adjuvant effects found in the ADP-ribosylating exotoxin.

TABLE 13

Antibody to Diphtheria

| Mouse Number | Immunizing Antigen | IgG ELISA Units |
|---|---|---|
| 4731 | DT + PT | 1,039 |
| 4732 | DT + PT | 1 |
| 4733 | DT + PT | 28 |
| 4734 | DT + PT | 15 |
| 4735 | DT + PT | 20 |
| 4621 | DT | 0 |
| 4622 | DT | 0 |
| 4623 | DT | 0 |
| 4624 | DT | 0 |
| 4625 | DT | 0 |

Example 14

BALB/c mice were immunized transcutaneously as described above for "Immunization Procedure", in groups of five mice. Mice were immunized once at 0 weeks with 50 μg of pertussis toxin per 100 μl of saline solution. The solution was vortexed for 10 seconds prior to immunization.

The antibodies were quantitated using ELISA as described for "ELISA IgG(H+L)". Anti-pertussis toxin antibodies were detected at 8 weeks in animals immunized with pertussis. The highest responder had anti-petussis toxin antibody ELISA units of 73. Thus, pertussis toxin acts as an adjuvant for itself and immunizes after a single immunization.

TABLE 14

Antibody to Pertussis

| Mouse Number | Immunizing Antigen | IgG ELISA Units |
|---|---|---|
| 4731 | PT | 56 |
| 4732 | PT | 60 |
| 4733 | PT | 3 |
| 4734 | PT | 13 |
| 4735 | PT | 73 |

Example 15

BALB/c mice were immunized transcutaneously as described above for "Immunization Procedure", in groups of five mice. Mice were immunized once at 0 weeks with 50 μg of tetanus toxoid and 100 μg of cholera toxin per 100 μl of saline solution. The solution was vortexed for 10 seconds prior to immunization.

The antibodies were quantitated using ELISA as described for "ELISA IgG(H+L)". Anti-tetanus toxoid antibodies were detected at 8 weeks in animal 5173 at 443 ELISA units.

Example 16

The possibility that oral immunization occurred through grooming after epicutaneous application and subsequent washing of the site of application was evaluated using $^{125}$I-labeled CT to track the fate of the antigen/adjuvant. Mice were anesthetized, transcutaneously immunized as described above for "Immunization Procedure" with 100 μg of $^{125}$I-labeled CT (150,000 cpm/μg CT). Control mice remained anesthetized for 6 hours to exclude grooming, and experimental mice were anesthetized for one hour and then allowed to groom after washing. Mice were sacrificed at 6 hours and organs weighed and counted for $^{125}$I on a Packard gamma counter. A total of 2–3 μg of CT was detected on the shaved skin at the site of immunization (14,600 cpm/μg tissue) while a maximum of 0.5 μg of CT was detected in the stomach (661 cpm/μg tissue) and intestine (9 cpm/μg tissue).

Oral immunization (n=S) with 10 μg if CT in saline at 0 and 3 weeks (without NaHCO$_3$) induced a 6 week mean IgG antibody response of <1,000 ELISA units whereas transcutaneous immunization with 100 μg of CT, shown above to result in less than 5 μg of CT retained in the skin after washing, resulted in an anti-CT response of 42,178 ELISA units at 6 weeks. Induction of an immune response to orally fed CT requires the addition of NaHCO$_3$ to the immunizing solution (Piece, 1978; Lycke and Holmgren, 1986). Thus, oral immunization does not significantly contribute to the antibodies detected when CT is applied epicutaneously to the skin.

Example 17

In vivo evidence of Langerhans cell activation was obtained using cholera toxin (CT) in saline applied epicutaneously to the skin, specifically the ears of the mouse, where large populations of Langerhans cells can be readily visualized (Enk et al., 1993; Bacci et al., 1997), and staining for major histocompatibility complex (MHC) class II molecules which is upregulated in activated Langerhans cells (Shimada et al., 1987).

BALB/c mouse ears were coated on the dorsal side with either 100 μg of CT in saline, 100 μg of CTB in saline, saline alone, or an intradermal injection of the positive controls 100 pg LPS or 10 μg TNFα, for one hour while the mouse was anesthetized. The ears were then throughly washed and, after 24 hours, the ears were removed and epidermal sheets were harvested and stained for MHC class II expression as described by Caughman et al. (1986). Epidermal sheets were stained with MKD6 (anti-I-A$^d$) or negative control Y3P (anti-I-A$^k$), and goat anti-mouse FITC F(ab)$_2$ was used as a second step reagent. Mice transcutaneously immunized on the ear (as described above without shaving) had previously been found to have anti-CT antibodies of 7,000 ELISA units three weeks after a single immunization.

Figure 1B:
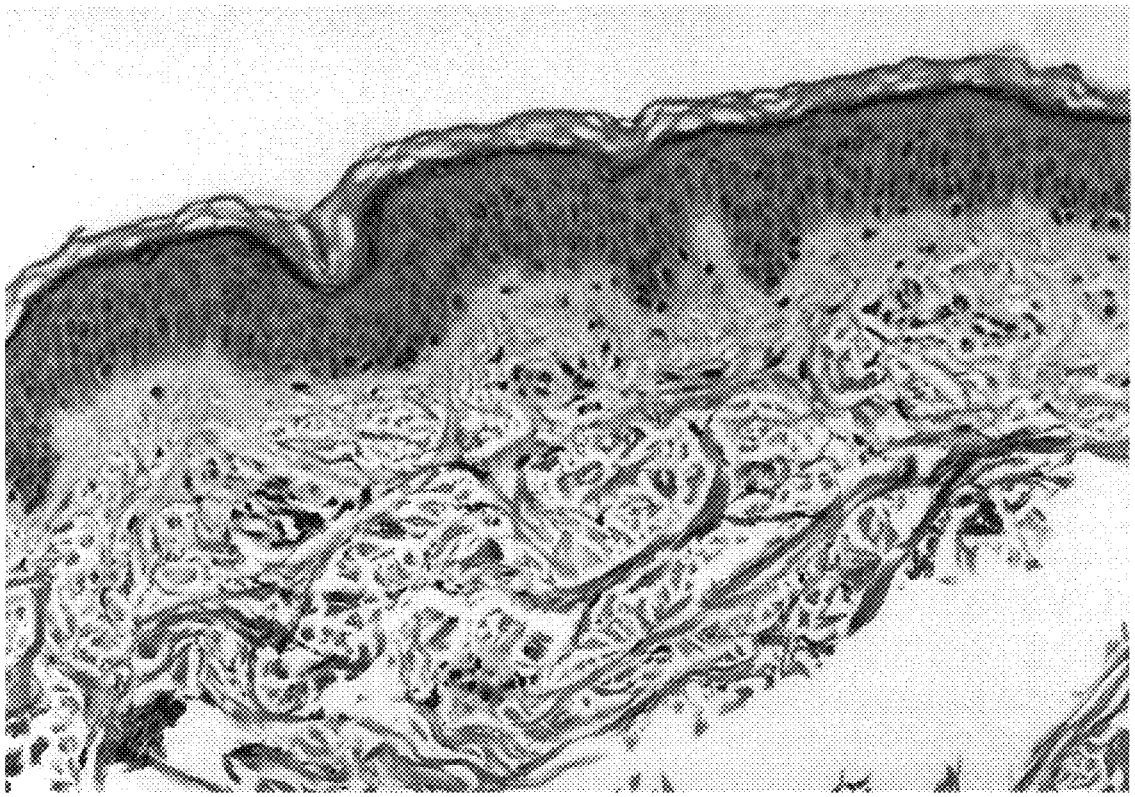
Figure 1C:
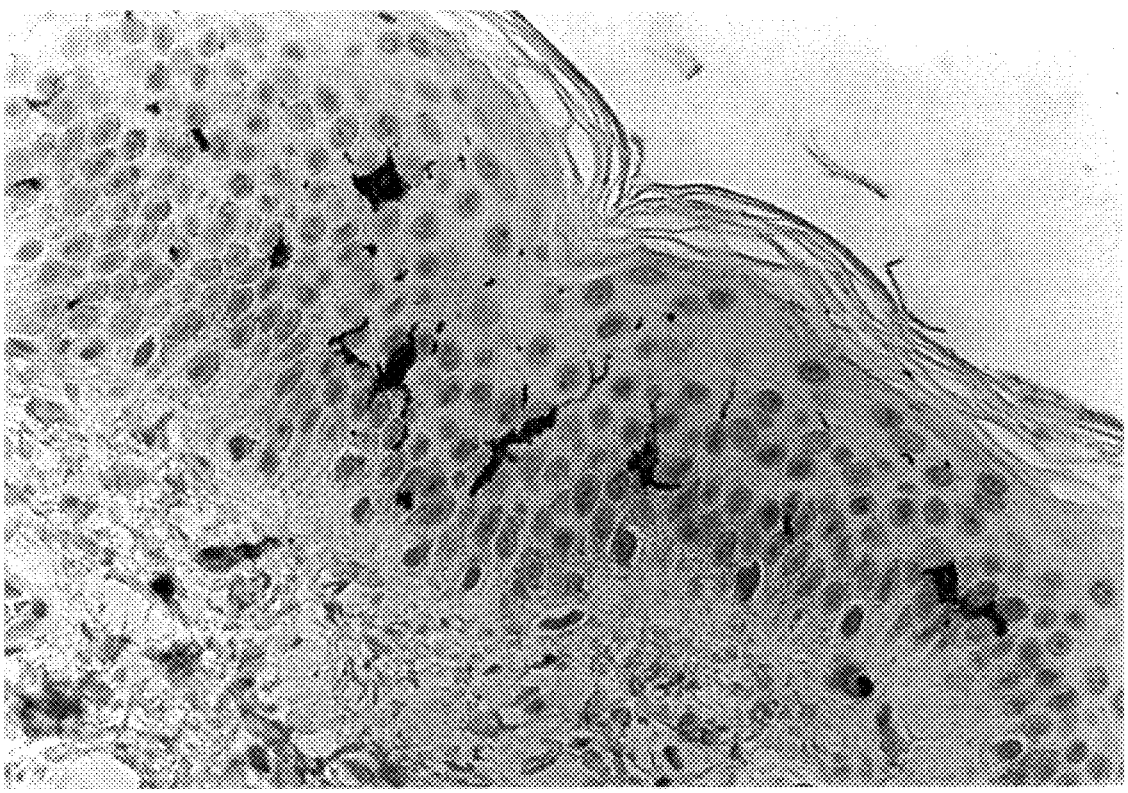
Figure 1D:
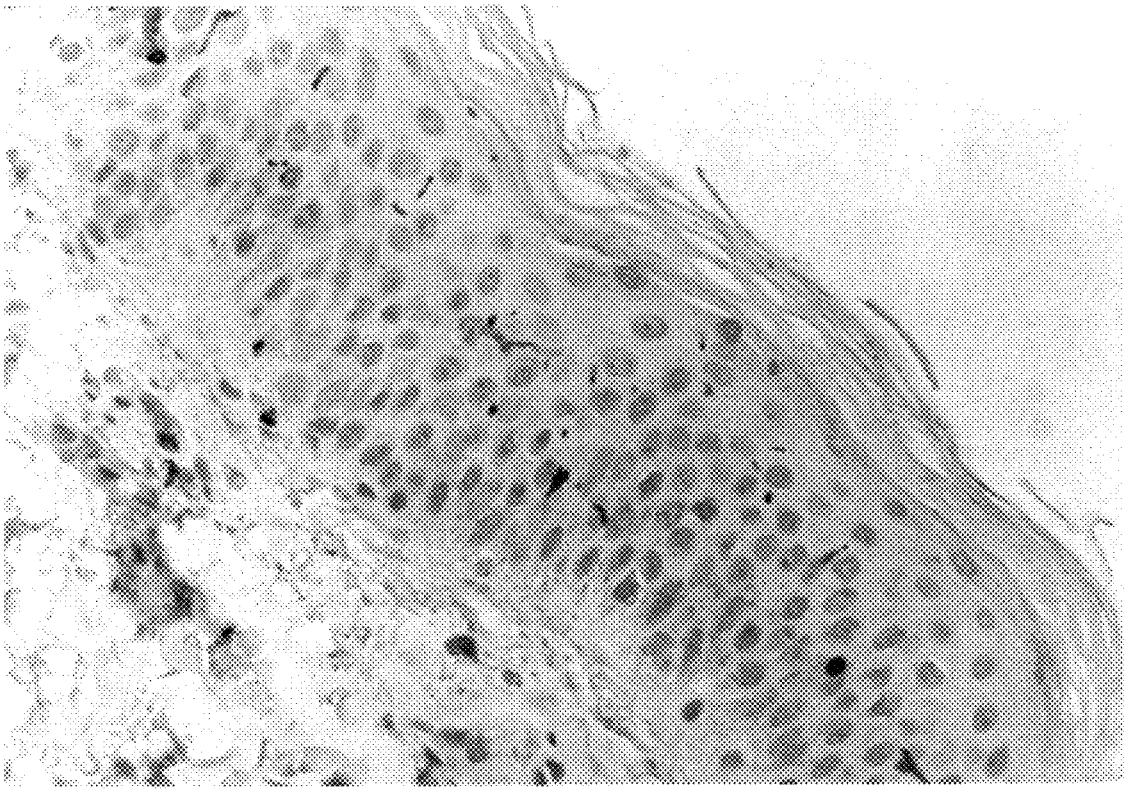
Figure 1E:
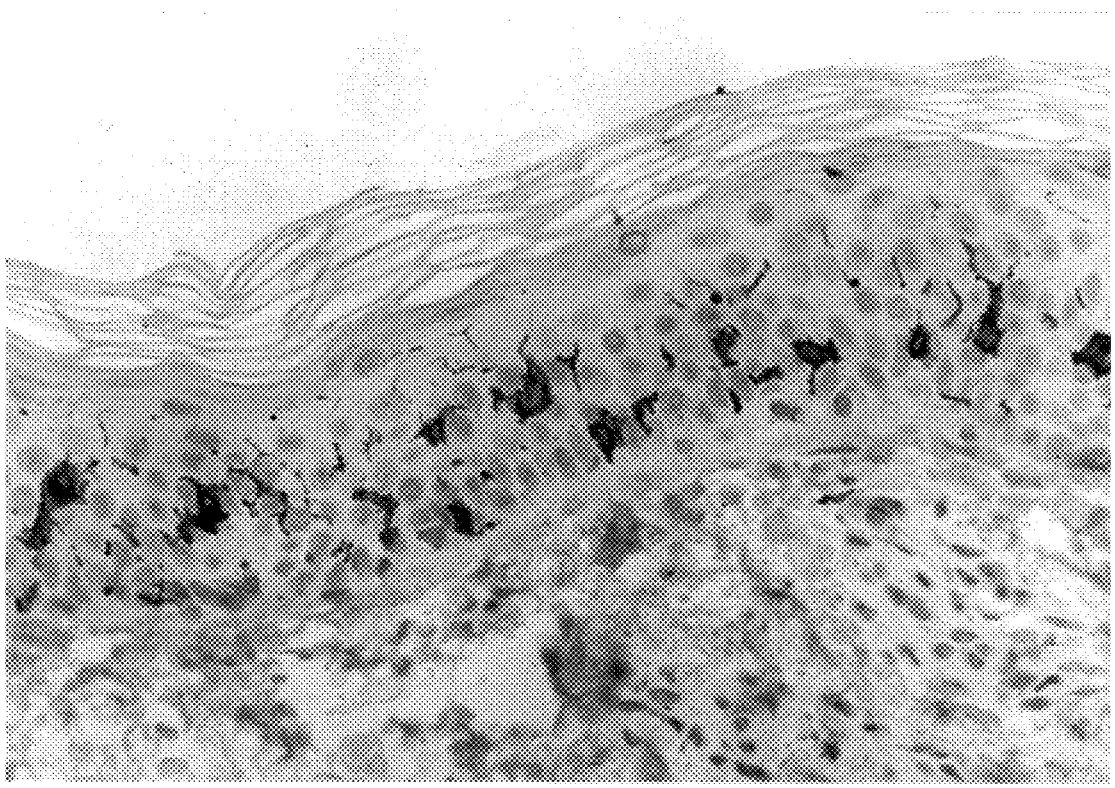
Figure 1F:
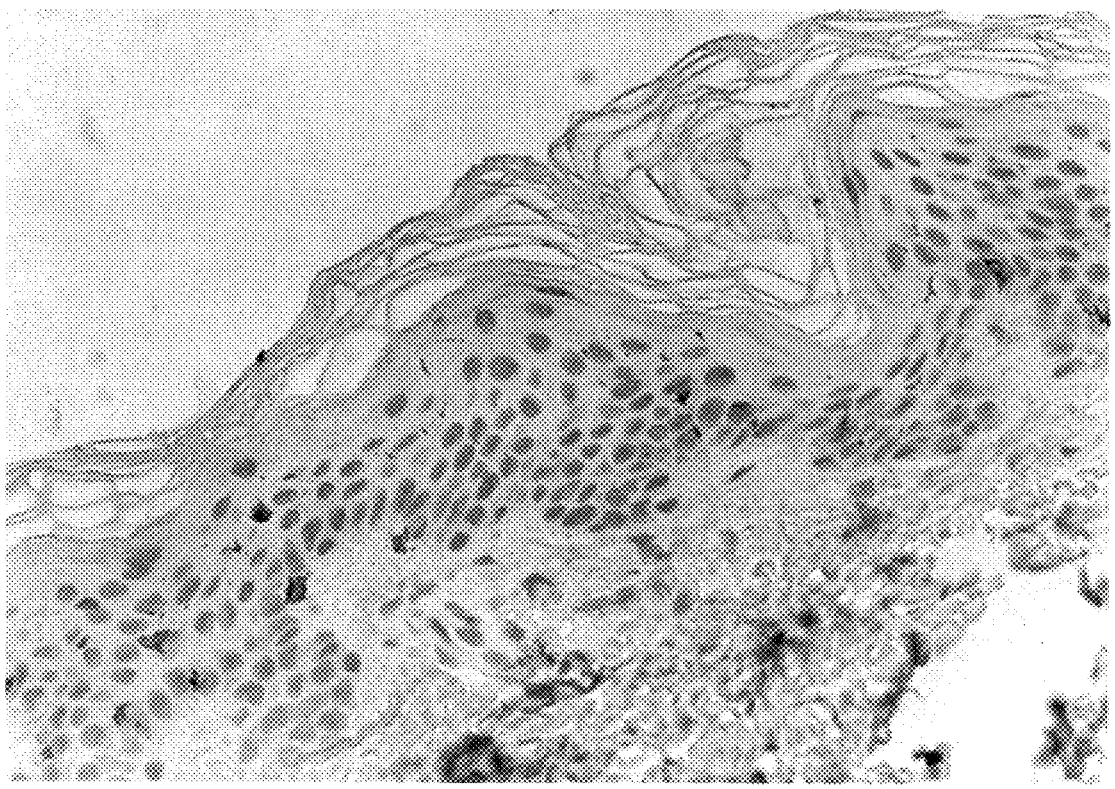
Figure 2A:
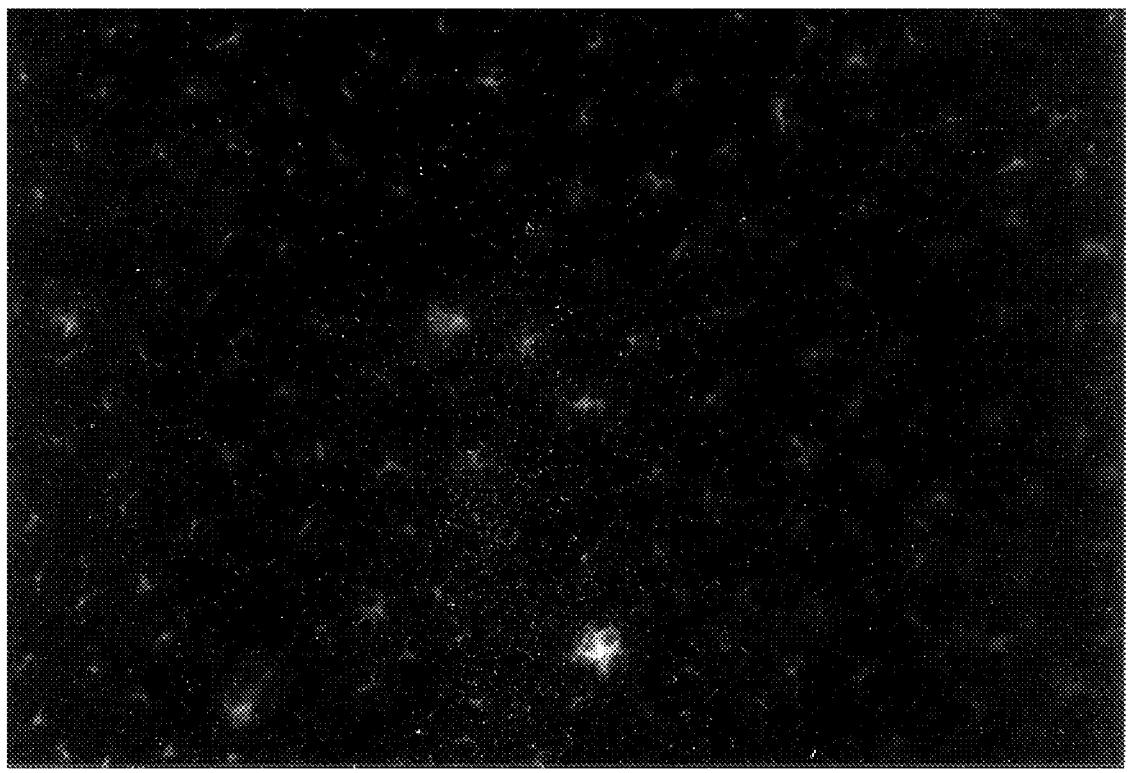
Figure 2B:
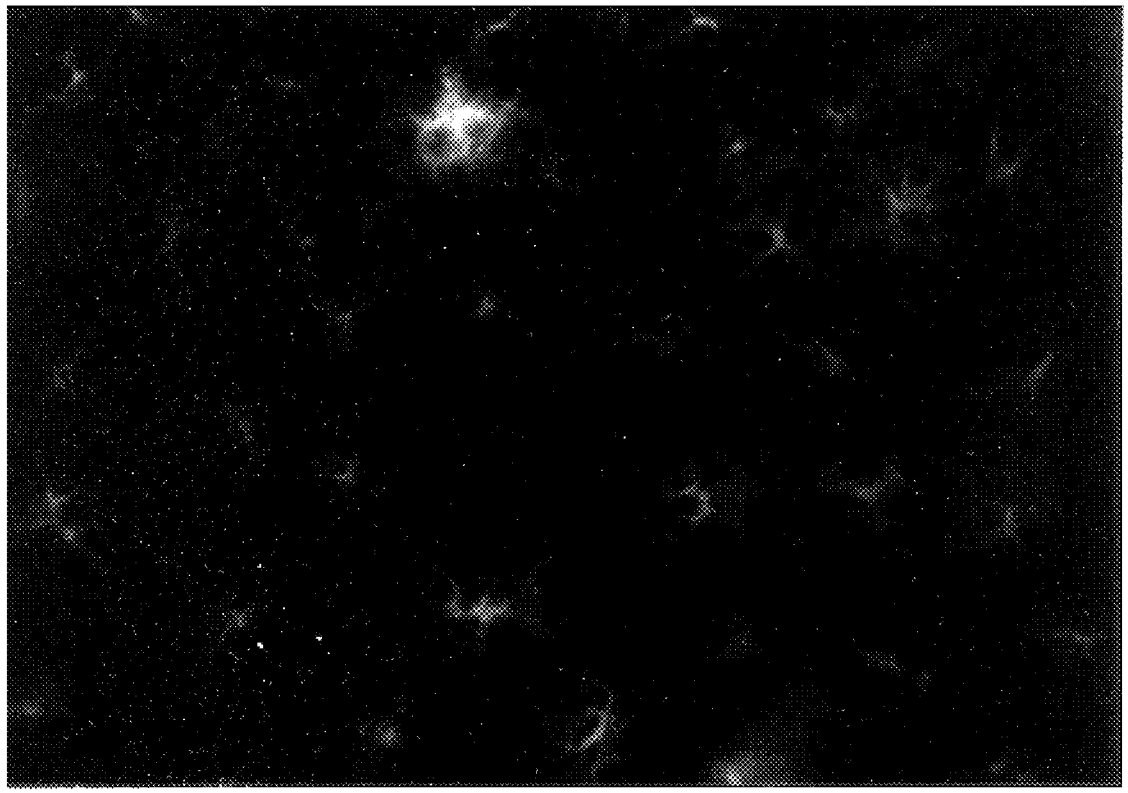
Figure 2C:
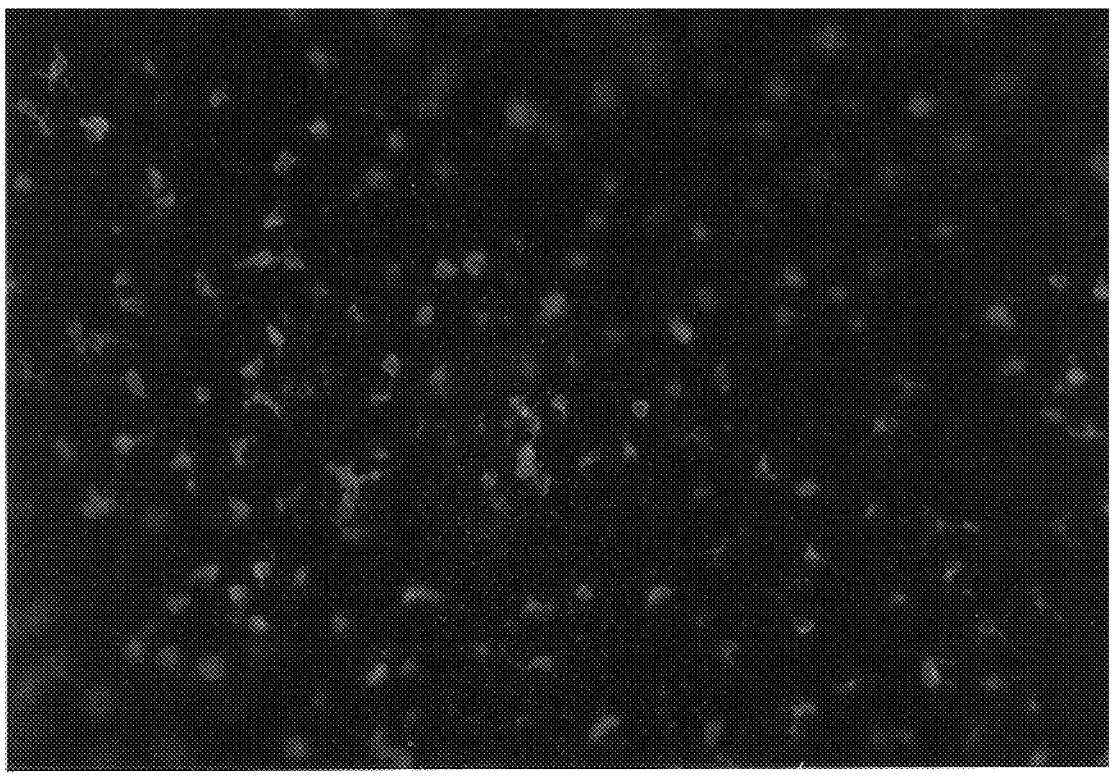
Figure 2D:
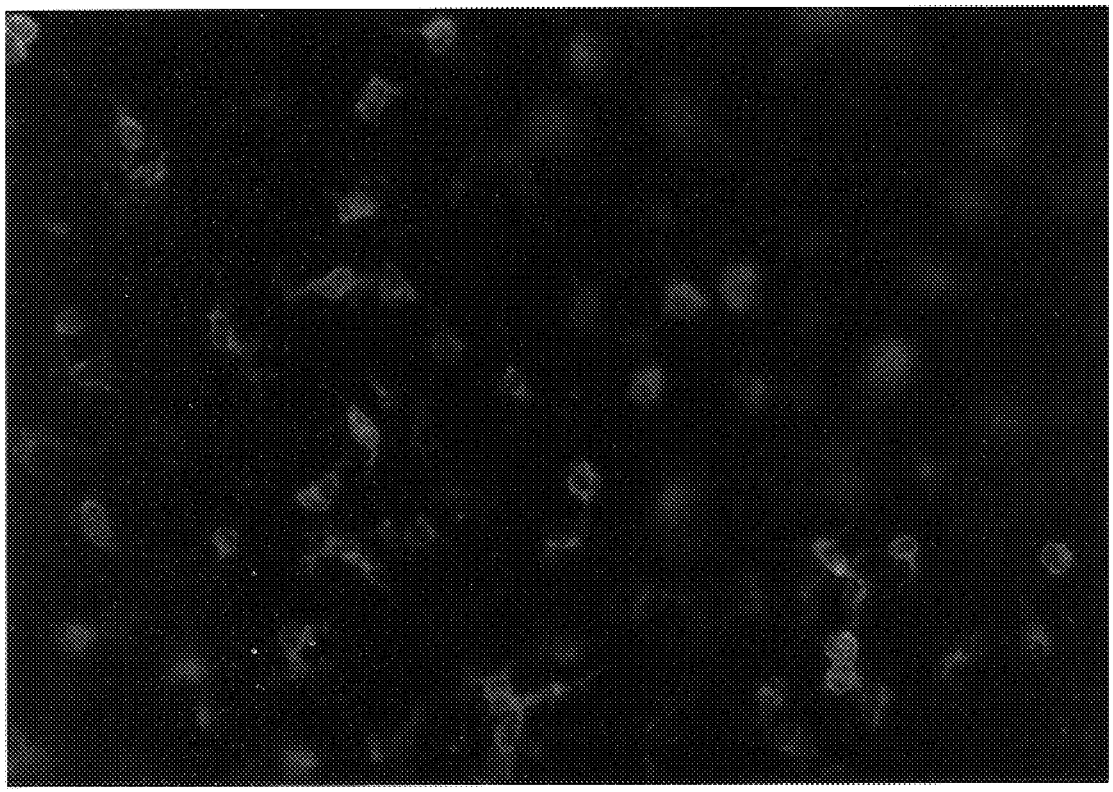

Enhanced expression of MHC class II molecules as detected by staining intensity, the reduced number of Langerhans cells (especially with cholera toxin), and changes in Langerhans cell morphology were found in the epidermal sheets of the mice immunized with CT and CTB comparable to controls (FIG. 1), suggesting that the Langerhans cells were activated by the epicutaneously applied cholera toxin (Aiba and Katz, 1990; Enk et al., 1993).

Example 18

Langerhans cells represent the epidermal contingent of a family of potent accessory cells termed 'dendritic cells'. Langerhans cells (and perhaps related cells in the dermis) are thought to be required for immune responses directed against foreign antigens that are encountered in skin. The 'life cycle' of the Langerhans cell is characterized by at least two distinct stages. Langerhans cells in epidermis (the 'sentinels') can ingest particulates and process antigens efficiently, but are weak stimulators of unprimed T cells. In contrast, Langerhans cells that have been induced to migrate to lymph nodes after contact with antigen in epidermis (the 'messengers') are poorly phagocytic and have limited antigen-processing capabilities, but are potent stimulators of naive T cells. If Langerhans cells are to fulfill both their 'sentinel' and 'messenger' roles, they must be able to persist in epidermis, and also be able to exit epidermis in a controlled fashion after exposure to antigen. Thus, regulation of Langerhans cell-keratinocyte adhesion represents a key control point in Langerhans cell trafficking and function. Langerhans cells express E-cadherin (Blauvelt et al., 1995), a homophilic adhesion molecule that is prominently represented in epithelia. Keratinocytes also express this adhesion molecule, and E-cadherin clearly mediates adhesion of murine Langerhans cells to keratinocytes in vitro. It is known that E-cadherin is involved in the localization of Langerhans cells in epidermis. See Stingl et al. (1989) for a review of the characterization and properties of Langerhans cells and keratinocytes.

The migration of epidermal Langerhans cells (LC) and their transport of antigen from the skin to draining lymph nodes are known to be important in the induction of cutaneous immune responses, such as contact sensitization. While in transit to the lymph nodes, Langerhans cells are subject to a number of phenotypic changes required for their movement from the skin and acquisition of the capacity for antigen presentation. In addition to the upregulation of MHC class II molecules, are alterations in the expression of adhesion molecules that regulate interactions with the surrounding tissue matrix and with T lymphocytes. The migration of the Langerhan cell is known to be associated with a marked reduction in the expression of E-cadherin (Schwarzenberger and Udey, 1996, and a parallel upregulation of ICAM-1 (Udey, 1997).

Transcutaneous immunization with bacterial ADP ribosylating exotoxins (bARE's) target the Langerhans cells in the epidermis. The bAREs activate the Langerhans cell, transforming it from its sentinel role to its messenger role. Ingested antigen is then taken to the lymph node where it is presented to B and T cells (Streilein and Grammer, 1989; Kripke et al., 1990; Tew et al., 1997). In the process, the epidermal Langerhans cell matures into an antigen-presenting dendritic cell in the lymph node (Schuler and Steinman, 1985); lymphocytes entering a lymph node segregate into B-cell follicles and T-cell regions. The activation of the Langerhans cell to become a migratory Langerhans cell is known to be associated with not only a marked increase in MHC class II molecules, but also marked reduction in the expression of E-cadherin, and upregulation of ICAM-1.

We envision that cholera toxin (CT) and its B subunit (CTB) upregulate the expression of ICAM-1 and downregulate the expression of E-cadherin on Langerhans cells as well as upregulate the expression of MHC class II molecules on the Langerhans cell. CT or CTB acts as an adjuvant by freeing the sentinel Langerhans cell to present antigens such as BSA or diphtheria toxoid phagocytosed by the Langerhans cell at the same location and time as the encounter with the CT or CTB when they are acting as adjuvant. The activation of a Langerhans cells to upregulate the expression of ICAM-1 and dowregulate the expression of E-cadherin may be mediated by cytokine release including TNFα and IL-1β from the epidermal cells or the Langerhans cells themselves.

This method of adjuvancy for transcutaneous immunization is envisioned to work for any compound that activates the Langerhans cell. Activation could occur in such manner as to downregulate the E-cadherin and upregulate ICAM-1. Langerhans cells would then carry antigens made of mixtures of such Langerhans cell-activating compounds and antigens (such as diphtheria toxoid or BSA) to the lymph nodes where the antigens are presented to T cells and evoke an immune response. Thus, the activating substance such as a bARE can be used as an adjuvant for an other wise transcutaneously non-immunogenic antigen such as Diphtheria toxoid by activating the Langerhans cell to phagocytose the antigen such as diphtheria toxoid, migrate to the lymph node, mature into a dendritic cell, and present the antigen to T cells.

The T-cell helper response to antigens used in transcutaneous immunization may be influenced by the application of cytokines and/or chemokines. For example, interleukin-10 (IL-10) may skew the antibody response towards a Th2 IgG1/IgE response whereas anti-IL-10 may enhance the production of IgG2a (Bellinghausen et al., 1996).

The disclosures of all patents, as well as all other printed documents, cited in this specification are incorporated herein by reference in their entirety.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims below.

REFERENCES

Aiba, S., and Katz, S. I. (1990) Phenotypic and functional characteristics of in vivo-activated Langerhans cells. J. Immunol., 145:2791–2796

Alving, C. R., et al. (1986) Effectiveness of liposomes as potential carriers of vaccines: Applications to cholera toxin and human malaria sporozoite antigen. Vaccine, 4:166–172.

Alving, C. R., and Wassef, N. M. (1994) Cytotoxic T lymphocytes induced by liposomal antigens: Mechanisms of immunological presentation. AIDS Res. *Hum. Retro.*, 10(sup. 2):S91–S94.

Alving, C. R., et al. (1993) The preparation and use of liposomes in immunological studies. In: *Liposome Technology*, vol. 3, (Ed., Gregoriadis, G.), CRC Press, Boca Raton, pp. 317–343.

Antel, J. P., et al. (1996) Immunotherapy for multiple sclerosis: From theory to practice. Nature Medicine, 2:1074–1075.

Ausubel, F. M., et al. (1996) *Current Protocols in Molecular Biology*, Wiley, New York.

Bacci, S., et al. (1997) High and low doses of haptens dictate whether dermal or epidermal antigen-presenting cells promote contact hypersensitivity. Eur. J. Immunol., 27:442–448.

Bathurst, I. C., et al. (1993) An experimental vaccine cocktail for *Plasmodium falciparum* malaria. Vaccine, 11:449–456.

Bellinghausen, I. et al. (1996) Epidermal cells enhance interleukin 4 and immunoglobulin E production after stimulation with protein allergen. J. Invest. Dermatol., 107:582–588.

Blauvelt, A., et al. (1995) Human Langerhans cells express E-cadherin. J. Invest. Dermatol., 104:293–296.

Blum, H. E. (1995) Variants of hepatitis B, C and D viruses: Molecular biology and clinical significance. Digestion, 56:85–95.

Bodanszky, M. (1993) *Peptide Chemistry*, Springer-Verlag, New York.

Bos, J. D. (1997) The skin as an organ of immunity. Clin. Exp. Immunol., 107 (suppl. 1):3–5.

Bowen, J. C., et al. (1994) Cholera toxin acts as a potent adjuvant for the induction of cytotoxic T-lymphocyte responses with non-replicating antigens. Immunology, 81:338–342.

Burnette, W. N., et al. (1994) Recombinant microbial ADP-ribosylating toxins of *Bordetella pertussis, Vibrio cholerae,* and enterotoxigenic *Escherichia coli*: Structure, function, and toxoid vaccine Development. In: *Bioprocess Technology*, (Eds. Burnette, W. N., et al.), pp. 185–203.

Caughman, S. W., et al. (1986) Ia+ murine epidermal Langerhans cells are deficient in surface expression of the class I major histocompatibility complex. Proc. Natl. Acad. Sci. U.S.A., 83:7438–7442.

Chang, S. P., et al. (1989) Generalized immunological recognition of the major merozoite surface antigen (gp 195) of *Plasmodium falciparum*. Proc. Natl. Acad. Sci. U.S.A., 86:6343–6347.

Chang, S. P., et al. (1992) A carboxyl-terminal fragment of *Plasmodium falciparum* gp195 expressed by a recombinant baculovirus induces antibodies that completely inhibit parasite growth. J. Immunol., 139:548–555.

Chang, S. P., et al. (1994) Regulation of antibody specificity to *Plasmodium falciparum* merozoite surface protein-1 by adjuvant and MHC haplotype. J. Immunol., 152:3483–3490.

Craig, S. W., and Cuatrecasas, P. (1975) Mobility of the cholera toxin receptors on rat lymphocyte membranes. Proc. Natl. Acad. Sci. U.S.A., 72:3384–2288.

Dahl, M. V. (1996) Atopic dermatitis. In: *Clinical Immunodermatology*, $3^{rd}$ Ed. Mosby, St. Louis, pp. 345–352.

Delenda, C., et al. (1994) Analysis of C-terminally truncated dengue 2 and dengue 3 virus envelope glycoproteins: Processing in insect cells and immunogenic properties in mice. J. Gen. Virol., 75:1569–1578.

Deprez, B., et al. (1996) Comparative efficiencies of simple lipopeptide constructs for in vivo induction of virus-specific CTL. Vaccine, 14:375–382.

Deutscher, M. P. (1990) *Guide to Protein Purification*, Academic Press, San Diego.

Dragunsky, E. M., et al. (1992) Experimental evaluation of antitoxic protective effect of new cholera vaccines in mice. Vaccine, 10:735–736.

Elson, C. O., and Dertzbaugh, M. T. (1994) Mucosal adjuvants. In: *Handbook of Mucosal Immunology* (Eds. Ogra, P. L., et al.) Academic Press, San Diego, p. 391.

Enk, A. H., et al. (1993) An essential role for Langerhans cell-derived IL-1 beta in the initiation of primary immune responses in skin. J. Immunol., 150:3698–3704.

Fonseca, B. A., et al. (1994) Recombinant vaccinia viruses co-expressing dengue-1 glycoproteins prM and E induce neutralizing antibodies in mice. Vaccine, 12:279–285.

Frankenburg, S., et al. (1996) Effective immunization of mice against cutaneous leishmaniasis using an intrinsically adjuvanted synthetic lipopeptide vaccine. Vaccine, 14:923–929.

Fries, L. F., et al. (1992a) Liposomal malaria vaccine in humans: A safe and potent adjuvant strategy. Proc. Natl. Acad. Sci. U.S.A., 89:358–362.

Fries, L. F., et al. (1992b) Safety, immunogenicity, and efficacy of a *Plasmodium falciparum* vaccine comprising a circumsporozoite protein repeat region peptide conjugated to *Pseudomonas aeruginosa* toxin A. Infect. Immun., 60:1834–1839.

Glenn, G. M., et al. (1995) Murine IgG subclass antibodies to antigens incorporated in liposomes containing lipid A. Immunol. Lett., 47:73–78.

Goeddel, D. V. (1990) *Gene Expression Technology*, Academic Press, San Diego.

Gregoriadis, G. (1993) *Liposome Preparation and Related Techniques,* 2nd Ed., CRC Press, Boca Raton.

Herrington, D. A., et al. (1991) Safety and immunogenicity of a recombinant sporozoite malaria vaccine against *Plasmodium vivax*. Am. J. Trop. Med. Hyg., 45:695–701.

Jahrling, P. B., et al. (1996) Passive immunization of Ebola virus-infected cynomolgus monkeys with immunoglobulin from hyperimmune horses. Arch. Virol. Suppl., 11:135–140.

Janeway, C. A., and Travers, P. (1996). *Immunobiology*, Churchill Livingstone, New York.

Janson, J.-C., and Ryden, L. (1989) *Protein Purification*, VCH, New York.

Katkov, W. N. (1996) Hepatitis vaccines. Med. Clin. North Am., 80:189–200.

Khusmith, S., et al. (1991) Protection against malaria by vaccination with sporozoite surface protein 2 plus CS protein. Science, 252:715–718.

Kounnas, M. Z., et al. (1992) The $\alpha_2$-macroglobulin receptor/low density lipoprotein receptor-related protein binds and internalizes Pseudomonas exotoxin A. J. Biol. Chem., 267:12420–12423.

Kriegler, M. (1990) *Gene Transfer and Expression*, Stockton Press, New York.

Kripke, M. L., et al. (1990) Evidence that cutaneous antigen-presenting cells migrate to regional lymph nodes during contact sensitization. J. Immunol., 145:2833–2838.

Krueger, K. M., and Barbieri, J. T. (1995) The family of bacterial ADP-ribosylating exotoxins. Clin. Microbiol. Rev., 8:34–47.

Lee, A., and Chen, M. (1994) Successful immunization against gastric infection with Helicobacter species: Use of a cholera toxin B-subunit-whole-cell vaccine. Infect. Immun., 62:3594–3597.

Leung, D. Y. (1997) Atopic dermatitis: Immunobiology and treatment with immune modulators. Clin. Exp. Immunol., 107 (Suppl. 1):25–30.

Lycke, N., and Holmgren, J. (1986) Strong adjuvant properties of cholera toxin on gut mucosal immune responses to orally presented antigens. Immunology, 59:301–308.

Lieberman, J. M., and Greenberg, D. P. (1996) Hepatitis A and B vaccines in children. Adv. Pediatr. Infect. Dis., 11:333–363.

Malik, A., et al. (1991) Human cytotoxic T lymphocytes against the *Plasmodium falciparum* circumsporozoite protein. Proc. Natl. Acad. Sci. U.S.A., 88:3300–3304.

Mast, E. E., and Krawczynski, K. (1996) Hepatitis E: An overview. Annu. Rev. Med., 47:257–266.

Migliorini, P., et al. (1993) Malaria vaccine: Immunization of mice with a synthetic T cell helper epitope alone leads to protective immunity. Eur. J. Immunol., 23:582–585.

Morein, B., and Simons, K. (1985) Subunit vaccines against enveloped viruses: Virosomes, micelles and other protein complexes. Vaccine, 3:83–93.

Murray, E. J. (1991) *Gene Transfer and Expression Protocols*. Humana Press, Clifton, N.J.

Nohria, A., and Rubin, R. H. (1994) Cytokines as potential vaccine adjuvants. Biotherapy, 7:261–269.

Paul, A., and Cevc, G. (1995) Noninvasive administration of protein antigens: Transdermal immunization with bovine serum albumin in transfersomes. Vaccine Res., 3:145–164.

Paul, A., et al. (1995) Transdermal immunization with large proteins by means of ultradeformable drug carriers. Eur. J. Immunol., 25:3521–3524, 1995.

Paul, W. E., and Seder, R. A. (1994) Lymphocyte responses and cytokines. Cell, 76:241–251.

Peguet-Navarro, J., et al. (1995) Inhibitory effect on human Langerhans cell antigen presenting function. Adv. Exp. Med. Biol., 378:359–361.

Pessi, A., et al. (1991) Lack of H-2 restriction of the *Plasmodium falciparum* (NANP) sequence as multiple antigen peptide, Eur. J. Immunol., 24:2273–2276.

Pierce, N. F. (1978) The role of antigen form and function in the primary and secondary intestinal immune responses to cholera toxin and toxoid in rats. J. Exp. Med., 148:195–206.

Pierce, N. F., and Reynolds, H. Y. (1974) Immunity to experimental cholera. I. Protective effect of humoral IgG antitoxin demonstrated by passive immunization. J. Immunol., 113:1017–1023.

Plotkin, S. A., and Mortimer Jr., E. A. (1994) Vaccines, 2nd Ed., W. B. Saunders, Philadelphia.

Porgador, A., et al. (1997) Intranasal immunization with CTL epitope peptides from HIV-1 or ovalbumin and the mucosal adjuvant cholera toxin induces peptide-specific CTLs and protection against tumor development in vivo. J. Immunol., 158:834–841.

Rappuoli, R., et al. (1995) Genetic detoxification of bacterial toxins: A new approach to vaccine development. Int. Archiv. Allergy Immunol., 108:327–333.

Rappuoli, R., et al. (1996) New vaccines against bacterial toxins. Adv. Exp. Med. Biol., 397:55–60.

Ribi, H. O., et al. (1988) Three-dimensional structure of cholera toxin penetrating a lipid membrane. Science, 239:1272–1276.

Richards, R. L., et al. (1995) A compendium of vaccine adjuvants and excipients. In: *Vaccine Design* (Eds., Powell, M. F., and Newman, M. J.), Plenum, New York.

Roberts, M. S., and Walker, M. (1993) Water, the most natural penetration enhancer. In: *Pharmaceutical Skin Penetration Enhancement* (Eds., Walters, K. A., and Hadgraft, J.), Marcel Dekker, New York.

Saloga, J., et al. (1996) Superantigens. Exp. Dermatol., 5:65–71.

Schneerson, R. E., et al. (1996) A toxoid vaccine for pertussis as well as diphtheria? Lessons to be relearned. Lancet 348:1289–1292.

Schuler, G., and Steinman, R. M. (1985) Murine epidermal Langerhans cells mature into potent immunostimulatory dendritic cells in vitro. J. Exp. Med., 161:526–546.

Schwarzenberger, K., and Udey, M. C. (1996) Contact allergens and epidermal proinflammatory cytokines modulate Langerhans cell E-cadherin expression in situ. J. Invest. Dermatol., 106:553–558.

Scopes, R. K. (1993) *Protein Purification*, Springer-Verlag, New York.

Seder, R. A., and Paul, W. E. (1994) Acquisition of lymphokine-producing phenotype by CD4+ T cells. Annu. Rev. Immunol., 12:635–673.

Shafara, A., et al. (1995) Hepatitis C. Ann. Intern. Med., 125:658–668.

Shankar, G., et al. (1996) Superantigen-induced Langerhans cell depletion is mediated by epidermal cell-derived IL-1$\alpha$ and TNF$\alpha$. Cell. Immunol., 171:240–245.

Skeiky, Y. A. W., et al. (1995) A recombinant Leishmania antigen that stimulates human peripheral blood mononuclear cells to express a Th1-type cytokine profile and to produce interleukin 12. J. Exp. Med., 181:1527–1537.

Smedile, A., et al. (1994) Advances in hepatitis D virus biology and disease. Prog. Liver Dis., 12:157–175.

Smucny, J. J., et al. (1995) Murine immunoglobulin G subclass responses following immunization with live dengue virus or a recombinant dengue envelope protein. Am. J. Trop. Med. Hyg., 53:432–437.

Stacey, K. J., et al. (1996) Macrophages ingest and are activated by bacterial DNA. J. Immunol., 157:2116–2122.

Stingl, G., et al. (1989) The immune functions of epidermal cells. Immunol. Ser., 46:3–42.

Streilein, J. W., and Grammer, S. F. (1989) In vitro evidence that Langerhans cells can adopt two functionally distinct forms capable of antigen presentation to T lymphocytes. J. Immunol., 143:3925–3933.

Summers, M. D., and Smith, G. E. (1987) A manual of methods for baculovirus vectors and insect cell culture procedure. Texas Agricultural Experiment Station Bulletin, No. 1555.

Tam, J. P. (1988) Synthetic peptide vaccine design: Synthesis and properties of a high-density multiple antigenic peptide system. Proc. Natl. Acad. Sci. U.S.A., 85:5409–5413.

Tew, J. G., et al. (1997) Follicular dendritic cells and presentation of antigen and costimulatory signals to B cells. Immunol. Rev., 156:39–52.

Trach, D. D., et al. (1997) Field trial of a locally produced, killed, oral cholera vaccine in Vietnam. Lancet, 349:231–235.

Udey, M. C. (1997) Cadherins and Langerhans cell immunobiology. Clin. Exp. Immunol., 107 (Suppl. 1):6–8.

Vandenbark, A. A., et al. (1996) Treatment of multiple sclerosis with T-cell receptor peptides: Results of a double-blind pilot trial. Nature Medicine, 2:1109–1115.

Vreden, S. G. S., et al. (1991) Phase I clinical trial of a recombinant malaria vaccine consisting of the circumsporozoite repeat region of Plasmodium falciparum coupled to hepatitus B surface antigen, Am. J. Trop. Med. Hyg., 45:533–538.

Wang, R., et al. (1995) Induction of protective polyclonal antibodies by immunization with a *Plasmodium yoelii* circumsporozoite protein multiple antigen peptide vaccine. J. Immunol., 154:2784–2793.

Wertz, P. W. (1992) Liposome dramatics: Chemicals aspects of the skin lipid approach. In: *Liposome Dramatics* (Eds., Braun-Falco, O. et al.), Springer-Verlag, New York, pp. 38–43.

White, K., et al. (1993) Induction of cytolytic and antibody responses using *Plasmodium falciparum* repeatless circumsporozoite protein encapsulated in liposomes. Vaccine, 11:1341–1346.

Wiesmueller, K.-H., et al. (1991) The antibody response in BALB/c mice to the *Plasmodium falciparum* circumsporozoite repetitive epitope covalently coupled to synthetic lipopeptide adjuvant. Immunology, 72:109–113.

Wisdom, G. B. (1994) *Peptide Antigens*, IRL Press, Oxford.

Zhang, T., et al. (1995) Oral immunization with the dodecapeptide repeat of the serine-rich Entamoeba histolytica protein (SREHP) fused to the cholera toxin B subunit induces a mucosal and systemic anti-SREHP antibody response. Infect. Immun., 63:1349–1355.

What we claim is:

1. A patch for transcutaneous immunization comprising:
   (a) a dressing, said dressing being configured to cause hydration of intact skin;
   (b) an immunizing antigen, and
   (c) an adjuvant; whereby application of the patch to said intact skin induces an immune response specific for said immunizing antigen.

2. The patch of claim 1, wherein the dressing is an occlusive dressing.

3. The patch of claim 1, wherein exposure of a Langerhans cell to the adjuvant activates the Langerhans cell.

4. The patch of claim 1, wherein exposure of a Langerhans cell to the adjuvant causes migration of the Langerhans cell to a lymph node.

5. The patch of claim 1, wherein exposure of a Langerhans cell to the adjuvant signals the Langerhans cell to mature into a dendritic cell.

6. The patch of claim 1, wherein the adjuvant is an ADP-ribosylating exotoxin.

7. The patch of claim 6, wherein the adjuvant is cholera toxin (CT) or cholera toxin B subunit (CTB).

8. The patch of claim 6, wherein the adjuvant is *E. coli* heat-labile enterotoxin (LT) or pertussis toxin.

9. The patch of claim 1, wherein the patch covers more than one draining lymph node field.

10. The patch of claim 1, wherein the adjuvant has a molecular mass greater than 500 daltons.

11. The patch of claim 1, wherein the adjuvant is one of the members selected from the group consisting of bacterial DNA, cytokines, chemokines, tumor necrosis factor alpha, genetically altered toxins, chemically conjugated bacterial ADP ribosylating exotoxins (bAREs) and lipopolysaccharides.

12. The patch of claim 1, wherein the adjuvant has a molecular mass greater than 800 daltons.

13. The patch of claim 1, wherein the adjuvant has a molecular mass greater than 1000 daltons.

* * * * *